US009809532B2

(12) United States Patent
Francis et al.

(10) Patent No.: US 9,809,532 B2
(45) Date of Patent: *Nov. 7, 2017

(54) USES OF HISTONE ACETYLTRANSFERASE ACTIVATORS

(75) Inventors: Yitshak Francis, New York, NY (US); Ottavio Arancio, New York, NY (US); Mauro Fa, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/125,214

(22) PCT Filed: Jun. 11, 2012

(86) PCT No.: PCT/US2012/041907

§ 371 (c)(1),
(2), (4) Date: Aug. 12, 2014

(87) PCT Pub. No.: WO2012/171008

PCT Pub. Date: Dec. 13, 2012

(65) Prior Publication Data

US 2014/0350116 A1    Nov. 27, 2014

Related U.S. Application Data

(60) Provisional application No. 61/495,495, filed on Jun. 10, 2011.

(51) Int. Cl.
*A61K 31/167* (2006.01)
*C07C 237/44* (2006.01)
*A61P 25/00* (2006.01)

(52) U.S. Cl.
CPC .......... *C07C 237/44* (2013.01); *A61K 31/167* (2013.01)

(58) Field of Classification Search
CPC ........................... A61K 31/167; C07C 237/44
USPC ................................. 514/620; 564/165, 168
See application file for complete search history.

(56) References Cited

U.S. PATENT DOCUMENTS

| 7,332,629 B2 | 2/2008 | Kundu et al. |
| 7,750,047 B2 | 7/2010 | Kundu et al. |
| 2004/0091967 A1 | 5/2004 | Kohler |
| 2005/0227915 A1 | 10/2005 | Steffan et al. |
| 2006/0018921 A1 | 1/2006 | Levenson et al. |
| 2006/0167107 A1 | 7/2006 | Kundu et al. |
| 2007/0265296 A1 | 11/2007 | Dalton et al. |
| 2008/0300205 A1 | 12/2008 | Tsai et al. |
| 2009/0076155 A1 | 3/2009 | Kundu et al. |
| 2009/0264414 A1 | 10/2009 | Andersen et al. |
| 2010/0168084 A1 | 7/2010 | Huber et al. |
| 2011/0081403 A1 | 4/2011 | Templeton |
| 2013/0121919 A1* | 5/2013 | Feng ..................... C07C 235/64 424/9.2 |

FOREIGN PATENT DOCUMENTS

| DE | 4428380 A1 | 2/1996 |
| EP | 1649852 A1 | 4/2006 |
| GB | 728098 A | 4/1955 |
| GB | 1436306 A | 5/1976 |
| WO | WO-2004/053140 A2 | 6/2004 |
| WO | WO-2005/121119 A1 | 12/2005 |
| WO | WO-2009/010454 A2 | 1/2009 |
| WO | WO-2011/072243 A1 | 6/2011 |

OTHER PUBLICATIONS

Unpublished co-pending U.S. Appl. No. 13/996,483.*
Abel, T. et al., "Epigenetic targets of HDAC inhibition in neurodegenerative and psychiatric disorders," Current Opinion in Pharmacology, vol. 8, pp. 57-64 (2008).
Alarcon, J. M. et al., "Chromatin Acetylation, Memory, and LTP Are Impaired in CBP+/−Mice: A Model for the Cognitive Deficit in Rubinstein-Taybi Syndrome and Its Amelioration," Neuron, vol. 42, No. 6, pp. 947-959 (Jun. 24, 2004).
Arancio, O. et al., "Neurotrophins, synaptic plasticity and dementia," Current Opinion in Neurobiology, vol. 17, Issue 3, pp. 325-330 (Jun. 2007).
Berge, S. et al., "Pharmaceutical Salts," Journal of Pharmaceutical Sciences, vol. 66, No. 1, pp. 1-19, (Jan. 1977).
Biel, M. et al., "Epigenetics—An Epicenter of Gene Regulation: Histones and Histone-Modifying Enzymes," Angewandte Chemie International Edition, vol. 44, Issue 21, pp. 3186-3216 (May 20, 2005).
Caccamo, A. et al., "CBP gene transfer increases BDNF levels and ameliorates learning and memory deficits in a mouse model of Alzheimer's disease," PNAS, vol. 107, No. 52, pp. 22687-22692 (Dec. 28, 2010).
Clements, A. et al., "Crystal structure of the histoen acetyltransferase domain of the human PCAF transcriptional regulator bound to coenzyme A," The EMBO Journal, vol. 18, pp. 3521-3532 (1999).
Conner, B. et al., "Brain-derived neurotrophic factor is reduced in Alzheimer's disease," Molecular Brain Research, vol. 49, Issue 1-2, pp. 71-81 (Oct. 3, 1997).
International Search Report and Written Opinion issued by the International Patent Office for Application No. PCT/US10/59925 dated May 9, 2011 (9 pages).
Corless, I.B. et al., "Predictors of Perception of Cognitive Functioning in HIV/AIDS," Journal of the Association of Nurses in AIDS care, vol. 11, Issue 3 pp. 19-26 (May-Jun. 2000).
Cowansage, K.K. et al., "Brain-Derived Neurotrophic Factor: A Dynamic Gatekeeper of Neural Plasticity," Current Molecular Pharmacology, vol. 3, pp. 12-29 (2010).
De La Cruz, X. et al., "Do protein motifs read the histone code?," Bioessays Review Articles, vol. 27, No. 2, pp. 164-175 (2005).
De Ruijter, A.J.M. et al., "Histone deacetylases (HDACs): characterization of the classical HDAC family," Biochem. J. Review Article, vol. 370, Part 3, pp. 737-749 (Mar. 15, 2003).
European Search Report issued by the European Patent Office for Application No. 11850544.5 dated Jul. 29, 2014 (8 pages).
Farah, M.J. et al., "Neurocognitive enhancement: What can we do and what should we do?," Nature Reviews Neuroscience, vol. 5, pp. 421-425 (May 2004).

(Continued)

*Primary Examiner* — Irina Neagu
(74) *Attorney, Agent, or Firm* — Wilmer Cutler Pickering Hale and Dorr LLP

(57) ABSTRACT

The invention provides methods for enhancing histone acylation, learning, memory and/or cognition in subjects with compound (I) or compositions comprising compound (I), or a pharmaceutically acceptable salt thereof.

6 Claims, 14 Drawing Sheets

(56) References Cited

OTHER PUBLICATIONS

Fischer, A. et al., "Recovery of learning and memory is associated with chromatin remodeling," Nature, vol. 447, No. 7141, pp. 178-182 (May 10, 2007).
Garzon, D.J. et al., "Oligomeric Amyloid Decreases Basal Levels of Brain-Derived Neurotrophic factor (BDNF) mRNA via Specific Downregulation of BDNF Transcripts IV and V in Differentiated Human Neuroblastoma Cells," The Journal of Neuroscience, vol. 27, No. 10, pp. 2628-2635 (Mar. 7, 2007).
Gould, Philip L., "Salt selection for basic drugs," International Journal of Pharmaceutics, vol. 33, Issues 1-3, pp. 201-217 (Nov. 1986).
Gregoretti, I.V. et al., "Molecular Evolution of the Histone Deacetylase Family: Functional Implications of Phylogenetic Analysis," J. Mol. Biol., vol. 338, No. 1, pp. 17-31 (2004).
Guan, J-S et al., "HDAC2 negatively regulates memory formation and synaptic plasticity," Nature Articles, vol. 459, pp. 55-60, 8 pages (May 7, 2009).
Gwack, Y. et al., "CREB-Binding Protein and Histone Deacetylase Regulate the Transcriptional Activity of Kaposi's Sarcoma-Associated Herpesvirus Open Reading Fram 50," Journal of Virology, vol. 75, No. 4, pp. 1909-1917 (Feb. 2001).
Hock, C. et al., "Region-Specific Neurotrophin Imbalances in Alzheimer Disease: Decreased Levels of Brain-Derived Neurotrophic Factor and Increased Levels of Nerve Growth Factor in Hippocampus and Cortical Areas," Arch Neurol, vol. 57, pp. 846-851 (2000).
International Search Report and Written Opinion issued by the International Search Authority for Application No. PCT/US12/41907, dated Sep. 21, 2012 (9 pages).
Kimura, A. et al., "A Decade of Histone Acetylation: Marking Eukaryotic Chromosomes with Specific Codes," J. Biochem., vol. 138, No. 6, pp. 647-662 (Dec. 2005).
Knutson, S.K. et al., "Liver-specific deletion of histone deacetylase 3 disrupts metabolic transcriptional networks," The EMBO Journal, vol. 27, No. 7, pp. 1017-1028 (Mar. 20, 2008).
Kornberg, R.D. et al., "Twenty-Five Years of the Nucleosome, Fundamental Particle of the Eukaryote Chromosome," Cell, vol. 98, pp. 285-294 (Aug. 6, 1999).
Lander, E.S. et al., "Initial sequencing and analysis of the human genome," Nature, vol. 409, pp. 860-921 (Feb. 15, 2001).
Lanni, C. et al., "Cognition enchancers between treating and doping the mind," Pharmacological Research, vol. 57, Issue 3, pp. 196-213 (Mar. 2008).
Lee, K.K. et al., "Histone acetyltransferase complexes: one size doesn't fit all," Nature Reviews Molecular Cell Biology, vol. 8, No. 4, pp. 284-295 (Apr. 2007).
Levenson, J.M. et al., "Regulation of Histone Acetylation during Memory Formation in the Hippocampus," The Journal of Biological Chemistry, vol. 279, No. 39, Issue of Sep. 24, pp. 40545-40559 (2004).
Lu, F. et al., "Chromatin Remodeling of the Kaposi's Sarcoma-Associated Herpesvirus ORF50 Promoter Correlates with Reactivation from Latency," Journal of Virology, vol. 77, No. 21, pp. 11425-11435 (Nov. 2003).
Mantelingu, K. et al., "Activation of p300 Histone Acetyltransferase by Small Molecules Altering Enzyme Structure: probed by Surface-Enhanced Raman Spectoscopy," The Journal of Physical Chemistry B, vol. 111, No. 17, pp. 4527-4534 (May 1, 2007).
Mao, X. et al., "GCN5 is a required cofactor for a ubiquitin ligase that targets NF-kB/RelA," Genes & Development, vol. 23, pp. 849-861 (2009).
Marmorstein, Ronen, "Structure of Histone Acetyltransferases," J. Mol. Biol., vol. 311, pp. 155-161, (2001).
NG, H.H. et al., "Histone deacetylases: silencers for hire," Trends in Biochemistry Sciences, vol. 25, No. 3, pp. 121-126 (Mar. 2000).
Peleg, S. et al., "Altered Histone Acetylation Is Associated with Age-Dependent Memory Impairment in Mice," Science, vol. 328, pp. 753-756, 6 pages (May 7, 2010).
Rakyan, V.K. et al., "The marks, mechanisms and memory of epigenetic states in mammals," Biochem. J., vol. 356, pp. 1-10 (2001).
Renaud, J. et al., "Estrogen Receptor Modulators: Identification and Structure-Activity Relationships of Potent ERα-selective tetrahydroisoquinoline ligands," Journal of Medicinal Chemistry, American Chemical Society, vol. 46, pp. 2945-2957 (Jan. 1, 2003).
Strahl, B.D. et al., "The language of covalent histone modifications," Nature, vol. 403, No. 6765, pp. 41-45, 5 pages (Jan. 6, 2000).
Sweatt, J. David, "Epigenetics and Cognitive Aging," Science, vol. 328, No. 5979, pp. 701-702 (May 7, 2010).
Yang, X-J et al., "HATs and HDACs: from structure, function and regulation to novel strategies for therapy and prevention," Oncogene, vol. 26, No. 37, pp. 5310-5318 (2007).
European Search Report issued by the European Patent Office for Application No. 12797614.0 dated Oct. 22, 2014 (6 pages).

\* cited by examiner

USES OF HISTONE ACETYLTRANSFERASE ACTIVATORS

This application is a National Stage Entry of International Application No. PCT/US2012/041907, filed on Jun. 11, 2012, which claims priority to U.S. Provisional Application No. 61/495,495, filed on Jun. 10, 2011, the entirety of the contents of each of which are incorporated herein by reference.

GOVERNMENT SUPPORT

This invention was made with government support under R01-NS049442 awarded by the National Institute of Neurological Disorders and Stroke (NINDS), and under AG034248 awarded by the National Institute of Aging (NIA). The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted in ASCII format via EFS-Web and is hereby incorporated by reference in its entirety. Said ASCII copy, created on Jul. 11, 2012, is named 1924931W.txt and is 31,182 bytes in size.

BACKGROUND OF THE INVENTION

Cognitive neurodegenerative disorders are characterized by synaptic dysfunction, cognitive abnormalities, and/or the presence of inclusion bodies throughout the CNS containing, for example, but not limited to native beta-amyloid fragments, native and phosphorylated Tau, native and phosphorylated alpha-synuclein, lipofuscin, cleaved TARDBP (TDB-43), in various percentages and in relation to the specific disease. Alzheimer's disease (AD) is one of the most prevalent neurodegenerative disorders characterized by memory loss, and significant research toward discovering treatment for this devastating disease has been undertaken.

Cognitive disorders that are not neurodegenerative, such as normal memory loss, as well as neurocognitive enhancement of normal individuals has become of increasing interest in the medical community (Farah, et al., *Nat. Rev. Neuroscience* 2004, 5, 421-425). Enhancement of learning and memory has been reported with amphetamines and derivatives thereof as well as other centrally-acting drugs. Certain nutritional supplements have also been reported to improve mental functions such as cognition and memory (Lanni, C., et al., *Pharmacol. Res.* 2004, 57, 196-213). However, many of these suffer from limited efficacy and/or untoward side effects due to their mechanisms of action.

Histone Acetyltransferases (HATs) are involved in histone acetylation (leading to gene activation), chromosome decondensation, DNA repair and non-histone substrate modification.

SUMMARY OF THE INVENTION

In one aspect, the invention is directed to methods and compositions for enhancing memory and learning in subjects.

In one aspect, the invention is directed to methods for increasing histone acetylation in a subject.

In one aspect, the invention is directed to methods for improving memory retention in a subject.

In one aspect, the invention is directed to methods for treating memory loss or a learning disabilty in a subject.

In some embodiments, the methods and compositions that are useful for treating, suppressing and/or preventing afflictions related to memory loss or learning disabilities in subjects.

In some embodiments, the methods comprise administering to the subject a therapeutically effective amount of compound (I),

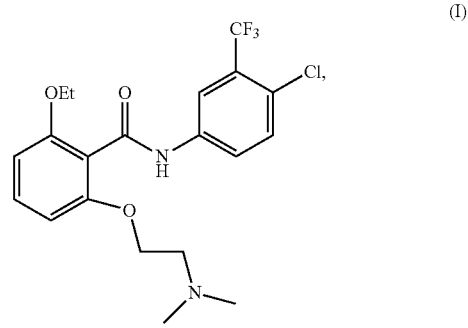 [SMILES: CCOc1cccc(OCCN(C)C)c1C(=O)Nc1ccc(Cl)c(C(F)(F)F)c1]

or a pharmaceutically acceptable salt thereof, or a composition comprising compound 1, or a pharmaceutically acceptable salt thereof, and a pharmaceutically acceptable carrier.

In some embodiments, the methods and compositions are useful for enhancing memory and/or learning in subjects. In some embodiments, the methods and compositions are useful for treating, suppressing and/or preventing afflictions related to memory loss or learning disabilities in subjects.

In some embodiments, the subject is not afflicted with a neurodegenerative disease. In some embodiments, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy.

In some embodiments, the present invention provides a method for enhancing memory in normal subjects. In some embodiments, the present invention provides for a method of improving learning in subjects. In some embodiments, the subject does not suffer from a neurodegenerative condition or disease.

In some embodiments, compound (I) increases histone acetylation. In some embodiments, histone acetylation comprises acetylation of histones H2B, H3, H4, or a combination thereof. In some embodiments, histone acetylation comprises acetylation of histone lysine residues H3K4, H3K9, H3K14, H4K5, H4K8, H4K12, H4K16, or a combination thereof.

In some embodiments, the subject is a mammal. In some embodiments, the subject is a mouse, rat, monkey, guniea pig, dog, or human. In some embodiments, the subject is a mouse, rat, monkey or human. In some embodiments, the subject is a mouse or a human. In some embodiments, the subject is a human.

In some embodiments, the methods reduce pain, anxiety or fear. In some embodiments, the methods reduce anxiety or fear. In some embodiments, the methods reduce anxiety. In some embodiments, the methods increase neurotransmission.

These and other embodiments of the invention are further described in the following sections of the application, including the Detailed Description, Examples, and Claims. Still other objects and advantages of the invention will become apparent by those of skill in the art from the disclosure herein, which are simply illustrative and not restrictive. Thus, other embodiments will be recognized by the ordinarily skilled artisan without departing from the spirit and scope of the invention.

DETAILED DESCRIPTION OF THE INVENTION

Figure 1:
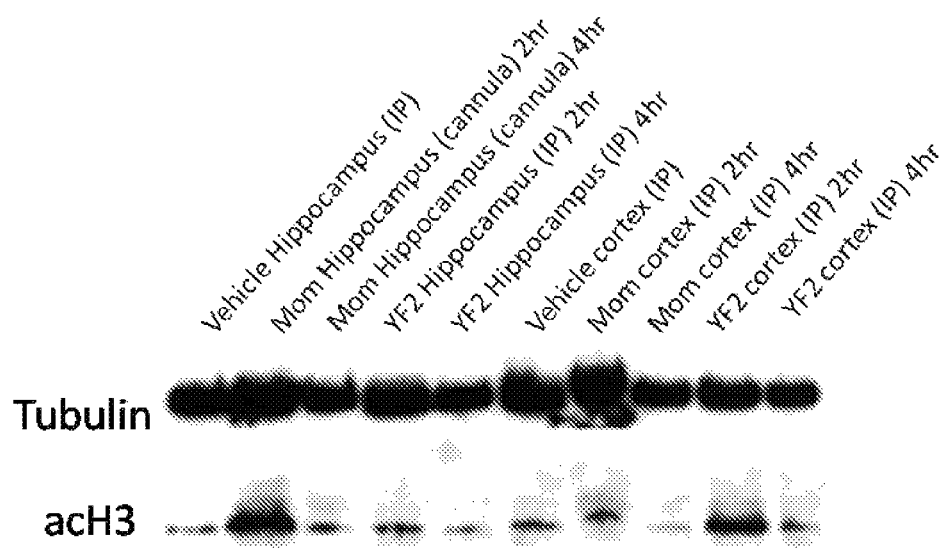
FIG. 1 is a photograph of a western blot showing acetylation levels of H3 in the cortex and hippocampus. Mice were administered with MOM via cannula (100 µg/µl per side) or mice were administered YF2 (Compound 1) (50 mg/kg, i.p.).

Memory is known to be modulated by epigenetics through regulation of gene expression. Epigenetics is defined as the mechanism that changes gene expression by 'marking' DNA or its associated proteins, through processes such as DNA methylation and histone (H) modification, without changing the DNA sequence itself (Rakyan, V. K., et al., *Biochem J.*, 2001. 356(Pt 1): p. 1-10; herein incorporated by reference in its entirety). Modification of histones by, for example, the addition or removal of acetyl or methyl functional groups causes the chromatin structure to open or close, so that the information contained within the DNA is made more or less accessible to transcription factors. Hence, deregulation of one of the epigenetic mechanisms might lead to memory disruption. For instance, reduction of histone acetylation causes the chromatin structure to close, so that the information contained within the DNA might be less accessible to transcription factors and memory formation (Rakyan, V. K., et al., *Biochem J.,* 2001. 356(Pt 1):1-10; herein incorporated by reference in its entirety).

The main strategy that is currently used to up-regulate histone acetylation involves inhibition of histone deacetylases (HDACs), enzymes that remove an acetyl group from histones. However, the pleiotropic effect of nonspecific HDAC inhibition may hamper the therapeutic potential of HDAC inhibitors (*J. Virol.* 2001. 75(4): 1909-17; *J. Virol.* 2003. 77(21): 11425-35; Knutson, S. K., *Biochemistry.* 2008, Vanderbilt: Nashville. 167; PLoS One, 2009. 4(8): p. e6612; each herein incorporated by reference in its entirety).

HATs share a highly conserved motif containing an acetyl-CoA binding site. Specific HAT activators are potential tools for pharmacological research and might find therapeutic applications. HAT activators have been reported; however these compounds are poorly soluble and poorly membrane permeant, and thus not considered acceptable drug candidates for the treatment of diseases and other afflictions. For example, N-(4-chloro-3-trifluoromethyl-phenyl)-2-ethoxy-benzamide is very poorly solubile in water and precipitated as soon as it was put in $H_2O$ (*J Phys Chem B,* 2007. 111(17): 4527-34).

In one aspect, the invention is directed to methods and compositions for enhancing memory and learning in subjects.

In one aspect, the invention is directed to methods for increasing histone acetylation in a subject.

In one aspect, the invention is directed to methods for improving memory retention in a subject.

In one aspect, the invention is directed to methods for treating memory loss or a learning disabilty in a subject In some embodiments, the methods and compositions that are useful for treating, suppressing and/or preventing afflictions related to memory loss or learning disabilities in subjects.

In some embodiments, the methods comprise administering to the subject a therapeutically effective amount of compound (I),

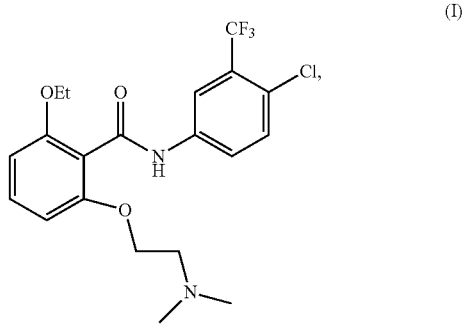 [SMILES: CCOc1cccc(OCCN(C)C)c1C(=O)Nc1ccc(Cl)c(C(F)(F)F)c1]

(I)

or a pharmaceutically acceptable salt thereof, or a composition comprising compound (I), or a pharmaceutically acceptable salt thereof, and a pharmaceutically acceptable carrier.

In some embodiments, the subject is not afflicted with a neurodegenerative disease. In one embodiment, the neurodegenerative disease comprises Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseasesm Progressive Supranuclear Palsy, Rett's syndrome, Tau-positive FrontoTemporal dementia, Tau-negative FrontoTemporal dementia, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, or Toxic encephalopathy.

In some embodiments, the present invention provides a method for enhancing memory in normal subjects. In some embodiments, the present invention provides for a method of improving learning in subjects. In some embodiments, the subject suffers from age-related memory impairment. In some embodiments, the subject does not suffer from a neurodegenerative condition. In some embodiments, the subject does not suffer from Alzheimer's Disease.

In some embodiments, the invention provides for memory enhancement in normal subjects. In some embodiments, the invention provides for memory enhancement and/or learning improvement in cognitively deficient subjects.

In some embodiments, the invention provides for memory enhancement in aging subjects. In some embodiments, the subject is greater than about 40 years old. In some embodiments, the subject is greater than about 45 years old, greater than about 50 years old, greater than about 55 years old, greater than about 60 years old, or greater than about 65 years old.

In some embodiments, the subject is a mammal. In some embodiments, the subject is a mouse, rat, monkey, guniea pig, dog, or human. In some embodiments, the subject is a mouse, rat, monkey or human. In some embodiments, the subject is a mouse or a human. In some embodiments, the subject is a human.

In some embodiments, the methods reduce pain, anxiety or fear. In some embodiments, the methods reduce anxiety or fear. In some embodiments, the methods reduce anxiety. In some embodiments, the methods increase neurotransmission.

In some embodiments, the invention provides for methods of treatment using compound I, which has histone acetyltransferase activity, HAT activation potency, high selectivity, reasonable pharmacokinetics and good permeability across the blood-brain-barrier (BBB).

In some embodiments, the methods increase gene expression in a subject resulting in enhanced memory and cognition.

Abbreviations and Definitions

The term "compound (I)" or "compound 1" as used herein means the compound designated as formula I or 1. It is also referred to herein as "YF2" or "OA2".

The term "composition(s) of the invention" as used herein means compositions comprising compound (I) or pharmaceutically acceptable salts thereof. The compositions of the invention may further comprise other agents such as, for example, excipients, stabilants, lubricants, solvents, and the like.

The term "method(s) of the invention" as used herein means methods comprising treatment with the compound (I) and/or compositions of the invention.

A "pharmaceutical composition" refers to a mixture of compound (I) described herein, or pharmaceutically acceptable salts thereof, with other chemical components, such as physiologically acceptable carriers and excipients. The purpose of a pharmaceutical composition is to facilitate administration of a compound to an organism.

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, for example sodium, potassium, calcium, ammonium or tetrafluoroborate. Exemplary pharmaceutically acceptable salts are found, for example, in Berge, et al. (*J. Pharm. Sci.* 1977, 66(1), 1 and Gould, P., *Int. J. Pharmaceutics* 1986, 33, 201-217; each herein incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of the memory loss or cognition, or one or more symptoms thereof, prevent the advancement of conditions related to memory loss or cognition, improve cognition, learning or memory in subjects not afflicted with a neurodegenerative disorder, or enhance or otherwise improve the prophylactic or therapeutic effect (s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in "Remington's Pharmaceutical Sciences" by E. W. Martin (hereby incorporated by reference in its entirety).

The terms "animal," "subject" and "patient" as used herein include all members of the animal kingdom including, but not limited to, mammals (e.g., mice, rats, cats, monkeys, dogs, horses, swine, etc.) and humans.

Acetylation and Methylation of DNA and Histones

Histone deacetylase (HDAC) and histone acetyltransferase (HAT) are enzymes that influence transcription by selectively deacetylating or acetylating the $\epsilon$-amino groups of lysine located near the amino termini of core histone proteins. Chromatin acetylation correlates with transcriptional activity (euchromatin), whereas deacetylation correlates with gene silencing. Interestingly, it was shown that increased acetylation of H3 in area CA1 of the hippocampus (an area in the brain that plays an important role in long-tem memory) occurs following associative memory. Additionally, by inhibiting HDAC, they were able to manipulate changes in the chromatin and enhance the formation of long-tem memory.

The DNA is firstly wrapped around an octamer complex of histones (H) to form nucleosomal units, giving the appearance of beads on a string (*Nature*, 2001. 409(6822): 860-921; herein incorporated by reference in its entirety). In turn, these nucleosomal units, fold into a higher-order chromatin fiber (*Cell*, 1999. 98(3): 285-94; herein incorporated by reference in its entirety). Each histone-octamer complex contains two copies of histones H3 and H4 bordered by two copies of histones 2A and 2B. Histone H1 and its avian variant H5 are linker histones that bind the nucleosome and both the entry and exit sites of the DNA, thus locking the DNA into place and allowing the formation of higher order structure. Every histone has a globular domain, which mediates histone-histone interactions, and an N-terminal 'tail' extension. The histone cores and in particular their tails, are targets for a considerable number of covalent modifications, such as acetylation, ubiquitination, sumoylation, phosphorylation, citrullination, ADP-ribosylation, and methylation (*Angew Chem Int Ed Engl*, 2005. 44(21): 3186-216; herein incorporated by reference in its entirety). Histone modifications associated with active gene transcription, such as H3 Lys4 methylation and H3 Lys56 acetylation, were found to lead to gene expression. On the other hand, histone modifications associated with the inactivation of gene transcription, such as H3 Lys27 methylation and H2A Lys 119 ubiquitination were found to cause gene silencing. Of particular interest for this application are histone 2B, 3 and 4 because they have been shown to be involved in memory processes (*Nature*, 2007. 447(7141): 178-82; *Neuron*, 2004. 42(6): 947-59; each herein incorporated by reference in its entirety). Studies of aging-associated memory dysfunction are discussed in *Science* 2010, 328, 701; herein incorporated by reference in its entirety.

HATs and HDACs. Histone modifications and their combinations have been proposed to be involved in gene regulation by modifying the chromatin accessibility and by acting as docking sites for transcription factors and modifying enzymes (*Bioessays*, 2005. 27(2): 164-75; *Nature*, 2000. 403(6765): 41-5; herein incorporated by reference in its entirety). One of the most studied histone modifications is the acetylation of the evolutionary-conserved lysine residues on the histone N-termini by histone acetyltransferase (HAT). In contrast, histone deacetylation, catalyzed by histone deacetylase (HDAC), was found to package the DNA into a more condensed form, limiting the access of transcription factors and thus acting as a gene silencer (*Trends Biochem Sci*, 2000. 25(3): 121-6; herein incorporated by reference in its entirety). The HATs involved in the regulation of gene expression include at least three groups of enzymes (*J Biochem*, 2005. 138(6): 647-62; herein incorporated by reference in its entirety). The general control non-derepressible 5 (Gcn5) is the founding member of the Gcn5 N-acetyltransferases (GNATs). The GNAT family members include Gcn5, PCAF, Elp3, HAT1m Hpa2 and Nut1. The MYST family is named after the founding members of the family: Morf, Ybf2, Sas2 and Tip60. In addition, other proteins including CBP/p300, Tafl and a number of nuclear receptor co-activators have been shown to possess intrinsic HAT activity. However, these proteins do not contain a consensus domain and therefore represent an 'orphan class' of HAT enzymes.

HDACs form repressor complexes with transcription activators and with other HDACs (*Biochem J*, 2003. 370(Pt 3): 737-49; herein incorporated by reference in its entirety). Mammalian HDACs can be divided into the classical and the silent information regulator 2 (Sir2)-related protein (sirtruin) families (*Oncogene*, 2007. 26(37): 5310-8; herein incorporated by reference in its entirety). In humans, members of the classical family have another subdivision, which include class I, II and IV, that share sequence similarity and require Zn+ for deacetylase activity. Class I HDACs (HDAC1-3, HDAC8) are related to the yeast gene repressor Rpd3p, and are subunits of at least two distinct co-repressor complexes, the Sin3 complex and the NuRD complex. Class II HDACs (HDAC4-7, 9 and 10) are similar to the yeast Hda1p HDAC, they act as gene repressors and have been implicated in various roles in cell differentiation and development. Class IV comprises HDAC11, which has some features of both class I and II HDACs. The sirtruin family includes class III HDACs (SIRT1-7), which are similar to yeast Sir2. Class III HDACs are biochemically and structurally distinct from the classical family and require $NAD^+$ as a cofactor. HDACs appear to be involved in gene silencing and heterochromatin formation at centromeres and telomeres (for a review see (*J Mol Biol*, 2004. 338(1):17-31; herein incorporated by reference in its entirety).

Alterations in epigenetic modifications including acetylation and methylation of DNA and histones may contribute to gene expression changes in cancer and neurological diseases. Addition of acetyl group on histones by Histone Acetyltransferases (HATs) enhances gene expression, while its removal by Histone Deacytylases (HDAC) reduces gene expression. Reduction in histone acetylation has been found in a variety of ailments such as tumors, mood disorders, and neurodegenerative diseases. Examples of HATs include, but are not limited to GCN5, GCN5L, PCAF, HAT1, ELP3, HPA2, ESA1, SAS2, SAS3, TIP60, HBO1, MOZ, MORF, MOF, SRC1, SRC3, TIF2, GRIP1, ATF-2 [see Lee and Workman (2007) Nat Rev Mol Cell Biol., 8(4):284-95, Marmorstein (2001) J Molec Biol. 311: 433-444; and Kimura et al., (2005) J Biochem. 138(6): 647-662; each of which are hereby incorporated by reference in their entireties]. In some embodiments, the HAT activator compound is directed to GCN5, GCN5L, HAT1, PCAF, or a combination thereof. In some embodiments, the HAT activator compound is directed to proteins that possess intrinsic HAT activity, such as nuclear receptor co-activators (for example, CBP/p300 and Tan). In some embodiments, the acetylation of H2, H3, and/or H4 histones is increased.

Increasing histone acetylation has been shown to improve outcome in a wide variety of diseases as diverse as asthma, infectious disease and psychiatric diseases. Although clinical trials of several HDAC inhibitors are currently underway, the alternative strategy where by histone acetylation is increased by HAT activation has not been extensively explored. For example, compounds in U.S. Patent Publication No. US2009076155 and PCT Publication No. WO2004053140 (each herein incorporated by reference in its entirety) have poor solubility and membrane permeability. Furthermore, the compounds disclosed in the patent applications do not disclose any data for the treatment of any diseases. Regulation of HAT is also discussed, for example, in U.S. Patent Publication No. US20040091967 and U.S. Pat. No. 7,750,047 (each herein incorporated by reference in its entirety).

No HAT activator is currently in drug trials, however several HDAC inhibitors are currently in clinical trials. Some of these HDAC inhibitors (HDACi) have shown therapeutic efficacy in preclinical trials. Without being bound by theory, it is believed that HAT activators may be useful drug candidates with a role similar to HDACi. However, previously available HAT activators had little solubility and membrane permeability, making them unsuitable as drugs.

Some HDACi are or were being developed for neurological diseases, such as an HDACi from Merck (Whitehouse Station, N.J.) that is being used for the treatment of neurodegenerative diseases; and HDACi from TopoTarget (Rockaway, N.J.) that was being used for the treatment of Huntington's disease, now discontinued; isovaleramide NPS-1776 (NPS Pharmaceutical, Bedminster, N.J.) that was being used for bipolar disorder, epilepsy, and migraines, now discontinued; and a histone acetyltransferase inhibitor for cancer from TopoTarget A/S (København, Denmark), which was discontinued in the preclinical stage. Histone Acylation is discussed in *Science* 2010, 328, 753 and *Nature* 2009, 459, 55; each herein incorporated by reference in its entirety.

Here, a HAT activator with improved solubility and membrane permeability is described and its potency in-vitro as well as in an animal model are shown. Compound (I) and other HAT activator compounds are also described in PCT/US10/59925, incorporated herein by reference in its entirety. In vitro and behavioral data show that HAT activator compound (I) can acetylate histone H3 in brain and ameliorate memory deficits in a mouse model of Alzheimer's disease. For example, compound (I) can be used as adjuvant therapy in several cancers, psychiatric and neurodegenerative diseases and may improve efficacy and safety of treatment for these disorders. Furthermore, the compound (I) exhibits good solubility and permeability of the Blood-Brain-Barrier (See Abel and Zukin (2008) Current Opinion in Pharmacology 8:57-64; and Lee and Workman (2007) Nat Rev Mol Cell Biol 8:284-295; each herein incorporated by reference in its entirety).

HAT1 is also known as KAT1 (K(lysine) acetyltransferase 1). The protein encoded by this gene is a type B histone acetyltransferase (HAT) that is involved in the rapid acetylation of newly synthesized cytoplasmic histones, which are in turn imported into the nucleus for de novo deposition onto nascent DNA chains. Histone acetylation, particularly of histone H4, plays an important role in replication-dependent chromatin assembly.

SEQ ID NO: 1 is the human wild type amino acid sequence corresponding to the HAT protein, the HAT 1 enzyme (residues 1-419):

```
  1  MAGFGAMEKF LVEYKSAVEK KLAEYKCNTN TAIELKLVRF
     PEDLENDIRT FFPEYTHQLF
 61  GDDETAFGYK GLKILLYYIA GSLSTMFRVE YASKVDENFD
     CVEADDVEGK IRQIIPPGFC
121  TNTNDFLSLL EKEVDFKPFG TLLHTYSVLS PTGGENFTFQ
     IYKADMTCRG FREYHERLQT
181  FLMWFIETAS FIDVDDERWH YFLVFEKYNK DGATLFATVG
     YMTVYNYYVY PDKTRPRVSQ
241  MLILTPFQGQ GHGAQLLETV HRYYTEFPTV LDITAEDPSK
     SYVKLRDFVL VKLCQDLPCF
301  SREKLMQGFN EDMAIEAQQK FKINKQHARR VYEILRLLVT
     DMSDAEQYRS YRLDIKRRLI
361  SPYKKKQRDL AKMRKCLRPE ELTNQMNQIE ISMQHEQLEE
     SFQELVEDYR RVIERLAQE
```

SEQ ID NO: 2 is the human wild type nucleotide sequence corresponding to HAT protein, the HAT1 enzyme (residues 1-1682), wherein the underscored ATG denotes the beginning of the open reading frame:

```
   1  ctgtgcggtc acttccggcc cgggagcgcg cgggttgatt
      cgtccttcct cagccgcggg
  61  tgatcgtagc tcggaaatgg cgggatttgg tgctatggag
      aaattttgg tagaatataa
 121  gagtgcagtg gagaagaaac tggcagagta caaatgtaac
      accaacacag caattgaact
 181  aaaattagtt cgttttcctg aagatcttga aaatgacatt
      agaactttct ttcctgagta
 241  tacccatcaa ctctttgggg atgatgaaac tgcttttggt
      tacaagggtc taaagatcct
 301  gttatactat attgctggta gcctgtcaac aatgttccgt
      gttgaatatg catctaaagt
 361  tgatgagaac tttgactgtg tagaggcaga tgatgttgag
      ggcaaaatta gacaaatcat
 421  tccacctgga ttttgcacaa acacgaatga tttcctttct
      ttactggaaa aggaagttga
 481  tttcaagcca ttcggaacct tacttcatac ctactcagtt
      ctcagtccaa caggaggaga
 541  aaactttacc tttcagatat ataaggctga catgacatgt
      agaggctttc gagaatatca
 601  tgaaaggctt cagaccttt tgatgtggtt tattgaaact
      gctagcttta ttgacgtgga
 661  tgatgaaaga tggcactact ttctagtatt tgagaagtat
      aataaggatg gagctacgct
 721  ctttgcgacc gtaggctaca tgacagtcta taattactat
      gtgtacccag acaaaacccg
 781  gccacgtgta agtcagatgc tgattttgac tccatttcaa
      ggtcaaggcc atggtgctca
 841  acttcttgaa acagttcata gatactacac tgaatttcct
      acagttcttg atattacagc
 901  ggaagatcca tccaaaagct atgtgaaatt acgagacttt
      gtgcttgtga agctttgtca
 961  agatttgccc tgttttccc gggaaaaatt aatgcaagga
      ttcaatgaag atatggcgat
1021  agaggcacaa cagaagttca aaataaataa gcaacacgct
      agaagggttt atgaaattct
1081  tcgactactg gtaactgaca tgagtgatgc cgaacaatac
      agaagctaca gactggatat
1141  taaaagaaga ctaattagcc catataagaa aaagcagaga
      gatcttgcta agatgagaaa
1201  atgtctcaga ccagaagaac tgacaaacca gatgaaccaa
      atagaaataa gcatgcaaca
1261  tgaacagctg gaagagagtt ttcaggaact agtggaagat
      taccggcgtg ttattgaacg
```

```
1321  acttgctcaa gagtaaagat tatactgctc tgtacaggaa
      gcttgcaaat tttctgtaca
1381  atgtgctgtg aaaaatctga tgactttaat tttaaaatct
      tgtgacattt tgcttatact
1441  aaaagttatc tatctttagt tgaatatttt cttttggaga
      gattgtatat tttaaaatac
1501  tgtttagagt ttatgagcat atattgcatt taaagaaaga
      taaagcttct gaaatactac
1561  tgcaattgct tcccttctta aacagtataa taaatgctta
      gttgtgatat gttaatgtgt
1621  gatgatatga ttcttaaata cttacaataa acctcattct
      taaatactta aaaaaaaaa
1681  aa
```

The polypeptide sequence of a HAT protein, human PCAF, is depicted in SEQ ID NO: 3. The nucleotide sequence of human PCAF is shown in SEQ ID NO: 4. Sequence information related to PCAF is accessible in public databases by GenBank Accession numbers NM_003884 (for mRNA) and NP_003875 (for protein). PCAF is also known as KAT2B (K(lysine) acetyltransferase 2B). CBP and p300 are large nuclear proteins that bind to many sequence-specific factors involved in cell growth and/or differentiation, including c-jun and the adenoviral oncoprotein E1A. The protein encoded by this gene associates with p300/CBP. It has in vitro and in vivo binding activity with CBP and p300, and competes with E1A for binding sites in p300/CBP. It has histone acetyl transferase activity with core histones and nucleosome core particles, indicating that this protein plays a direct role in transcriptional regulation.

SEQ ID NO: 3 is the human wild type amino acid sequence corresponding to the HAT protein, the PCAF enzyme (residues 1-832):

```
  1   MSEAGGAGPG GCGAGAGAGA GPGALPPQPA ALPPAPPQGS
      PCAAAAGGSG ACGPATAVAA
 61   AGTAEGPGGG GSARIAVKKA QLRSAPRAKK LEKLGVYSAC
      KAEESCKCNG WKNPNPSPTP
121   PRADLQQIIV SLTESCRSCS HALAAHVSHL ENVSEEEMNR
      LLGIVLDVEY LFTCVHKEED
181   ADTKQVYFYL FKLLRKSILQ RGKPVVEGSL EKKPPFEKPS
      IEQGVNNFVQ YKFSHLPAKE
241   RQTIVELAKM FLNRINYWHL EAPSQRRLRS PNDDISGYKE
      NYTRWLCYCN VPQFCDSLPR
301   YETTQVFGRT LLRSVFTVMR RQLLEQARQE KDKLPLEKRT
      LILTHFPKFL SMLEEEVYSQ
361   NSPIWDQDFL SASSRTSQLG IQTVINPPPV AGTISYNSTS
      SSLEQPNAGS SSPACKASSG
421   LEANPGEKRK MTDSHVLEEA KKPRVMGDIP MELINEVMST
      ITDPAAMLGP ETNFLSAHSA
481   RDEAARLEER RGVIEFHVVG NSLNQKPNKK ILMWLVGLQN
      VFSHQLPRMP KEYITRLVFD
541   PKHKTLALIK DGRVIGGICF RMFPSQGFTE IVFCAVTSNE
      QVKGYGTHLM NHLKEYHIKH
601   DILNFLTYAD EYAIGYFKKQ GFSKEIKIPK TKYVGYIKDY
      EGATLMGCEL NPRIPYTEFS
661   VIIKKQKEII KKLIERKQAQ IRKVYPGLSC FKDGVRQIPI
      ESIPGIRETG WKPSGKEKSK
721   EPRDPDQLYS TLKSILQQVK SHQSAWPFME PVKRTEAPGY
      YEVIRFPMDL KTMSERLKNR
781   YYVSKKLFMA DLQRVFTNCK EYNPPESEYY KCANILEKFF
      FSKIKEAGLI DK
```

SEQ ID NO: 4 is the human wild type nucleotide sequence corresponding to HAT protein, the PCAF enzyme (residues 1-4824), wherein the underscored ATG denotes the beginning of the open reading frame:

```
  1   gcggaaaaga ggccgtgggg ggcctcccag cgctggcaga
      caccgtgagg ctggcagccg
 61   ccggcacgca cacctagtcc gcagtcccga ggaacatgtc
      cgcagccagg gcgcggagca
121   gagtcccggg caggagaacc aagggagggc gtgtgctgtg
      gcggcggcgg cagcggcagc
181   ggagccgcta gtcccctccc tcctggggga gcagctgccg
      ccgctgccgc cgccgccacc
241   accatcagcg cgcggggccc ggccagagcg agccgggcga
      gcggcgcgct aggggaggg
301   cggggcgggg gaggggggtg ggcgaagggg gcgggagggc
      gtgggggag ggtctcgctc
361   tcccgactac cagagcccga gagggagacc ctggcggcgg
      cggcggcgcc tgacactcgg
421   cgcctcctgc cgtgctccgg ggcggcatgt ccgaggctgg
      cggggccggg ccgggcggct
481   gcggggcagg agccggggca ggggccgggc cgggggcgct
      gccccgcag cctgcggcgc
541   ttccgcccgc gcccccgcag ggctccccct gcgccgctgc
      cgccggggc tcggcgcct
```

-continued

```
 601 gcggtccggc gacggcagtg gctgcagcgg gcacggccga
     aggaccggga ggcggtggct
 661 cggcccgaat cgccgtgaag aaagcgcaac tacgctccgc
     tccgcgggcc aagaaactgg
 721 agaaactcgg agtgtactcc gcctgcaagg ccgaggagtc
     ttgtaaatgt aatggctgga
 781 aaaaccctaa ccccctcaccc actcccccca gagccgacct
     gcagcaaata attgtcagtc
 841 taacagaatc ctgtcggagt tgtagccatg ccctagctgc
     tcatgtttcc cacctggaga
 901 atgtgtcaga ggaagaaatg aacagactcc tgggaatagt
     attggatgtg aatatctct
 961 ttacctgtgt ccacaaggaa gaagatgcag ataccaaaca
     agtttatttc tatctattta
1021 agctcttgag aaagtctatt ttacaaagag gaaaacctgt
     ggttgaaggc tctttggaaa
1081 agaaaccccc atttgaaaaa cctagcattg aacagggtgt
     gataactttt gtgcagtaca
1141 aatttagtca cctgccagca aaagaaaggc aaacaatagt
     tgagttggca aaaatgttcc
1201 taaaccgcat caactattgg catctggagg caccatctca
     acgaagactg cgatctccca
1261 atgatgatat ttctggatac aaagagaact acacaaggtg
     gctgtgttac tgcaacgtgc
1321 cacagttctg cgacagtcta cctcggtacg aaaccacaca
     ggtgtttggg agaacattgc
1381 ttcgctcggt cttcactgtt atgaggcgac aactcctgga
     acaagcaaga caggaaaaag
1441 ataaaactgcc tcttgaaaaa cgaactctaa tcctcactca
     tttcccaaaa tttctgtcca
1501 tgctagaaga agaagtatat agtcaaaact ctcccatctg
     ggatcaggat tttctctcag
1561 cctcttccag aaccagccac ctaggcatcc aaacagttat
     caatccacct cctgtggctg
1621 ggacaatttc atacaattca acctcatctt cccttgagca
     gccaaacgca gggagcagca
1681 gtcctgcctg caaagcctct tctggacttg aggcaaaccc
     aggagaaaag aggaaaatga
1741 ctgattctca tgttctggag gaggccaaga aaccccgagt
     tatgggggat attccgatgg
1801 aattaatcaa cgaggttatg tctaccatca cggaccctgc
     agcaatgctt ggaccagaga
1861 ccaatttct gtcagcacac tcggccaggg atgaggcggc
     aaggttggaa gagcgcaggg
1921 gtgtaattga atttcacgtg gttggcaatt ccctcaacca
     gaaaccaaac aagaagatcc
1981 tgatgtggct ggttggccta cagaacgttt tctcccacca
     gctgccccga atgccaaaag
2041 aatacatcac acggctcgtc tttgacccga acacaaaac
     ccttgcttta attaaagatg
2101 gccgtgttat tggtggtatc tgtttccgta tgttcccatc
     tcaaggattc acagagattg
2161 tcttctgtgc tgtaacctca aatgagcaag tcaagggcta
     tggaacacac ctgatgaatc
2221 atttgaaaga atatcacata aagcatgaca tcctgaactt
     cctcacatat gcagatgaat
2281 atgcaattga atactttaag aaacagggtt tctccaaaga
     aattaaaata cctaaaacca
2341 aatatgttgg ctatatcaag gattatgaag gagccacttt
     aatgggatgt gagctaaatc
2401 cacgatcccc gtacacagaa ttttctgtca tcattaaaaa
     gcagaaggag ataattaaaa
2461 aactgattga agaaaacag gcacaaattc gaaaagttta
     ccctggactt tcatgtttta
2521 aagatggagt tcgacagatt cctatagaaa gcattcctgg
     aattagagag acaggctgga
2581 aaccgagtgg aaaagagaaa agtaaagagc ccagagaccc
     tgaccagctt tacagcacgc
2641 tcaagagcat cctccagcag gtgaagagcc atcaaagcgc
     ttggcccttc atggaacctg
2701 tgaagagaac agaagctcca ggatattatg aagttataag
     gttccccatg gatctgaaaa
2761 ccatgagtga acgcctcaag aataggtact acgtgtctaa
     gaaattattc atggcagact
2821 tacagcgagt cttttaccaat tgcaaagagt acaaccccc
     tgagagtgaa tactacaaat
2881 gtgccaatat cctggagaaa ttcttcttca gtaaaattaa
     ggaagctgga ttaattgaca
2941 agtgatttt tttcccctct gcttcttaga aactcaccaa
     gcagtgtgcc taaagcaagg
```

```
-continued
3001  tggtttagtt ttttacaaag aattggacat gatgtattga
      agagacttgt aaatgtaata
3061  attagcactt tgaaaaaac aaaaaacctc cttttagctt
      ttcagatatg tatttaaatt
3121  gaagtcatag gacatttta ttttatggaa tagattttaa
      tctatttact actattaagg
3181  taaattttct atggcatgtc cattagctat ttcatgatag
      atgattaggg gtttcctcaa
3241  aacctgtgtg tgaggaaatt gcacacagta gcaaaatttg
      gggaaatcca taacattttc
3301  agaccatgaa tgaatgtttc cattttttc taatggaatg
      tgagagttta cttttatttt
3361  attctgaagg acttttaagga agggatacat gattttaaaa
      aagcctgtaa gaggtgaaat
3421  atgtgatgtt tgaagtctct ttatagactt tttatatata
      ttttttaaaa cactcatcta
3481  gatgaggtgc tttgagcagt tctgaaaaat gcagttccag
      gaaagcaact gctttggttc
3541  ctaaggaaga aattctaaat aatgcaaact tttaaaataa
      gcatctaggt ttttgataat
3601  tctgtctact tacaacaaac ttgttagtac ataaccacta
      ttttaataat tatttctct
3661  acacaaatgt gtaatatcat atttgacttt gcttatgcag
      gccataagtt ccaaaagata
3721  atttccctgc ccacaaaggc ataaacttga aaacacatga
      gattgaatca acatgcttta
3781  ataggaaaag atgtatggtc tatatatgta tcaatctggt
      gaatcctcgt tctaataaag
3841  gttcttttc ttttctatga tacacacagc cacgctgata
      atatgcaaat gaacatttc
3901  ctttatgtct ctccagataa tgtttattgt ctgaggtaaa
      ttaaattccc accagggttt
3961  gctgtcagta ttttaacacc cacattagta tatgcgtcca
      gggtcataac cccctaaaat
4021  ccatcatgca acctattaa tctgtcttgg gattccagtt
      tagtgcttgg atttatttcc
4081  tgattacact acatagaaaa gtgagacatc tgccattccc
      aactctggga aaaccaacta
4141  atatacaacc atataaatga aggccatctt gatggtctca
      acactaattt ttatgatgca
```

```
-continued
4201  aatttataca ctgattttg taaaggacaa agttttaaaa
      gcgtatttaa cttgatgttt
4261  tctatcagca taaataaaat ggtcatgaat agtcattaaa
      aacagttgcc agtgataatc
4321  tgcatgaagg aaaaagaacc ctgcaaatgg ctattgagtt
      ggaagtattg ttttttgatat
4381  gtaagagata ttcagaatgc tcacactgaa aatgcctcaa
      cttttaaag tgtaagaaac
4441  caccatgagt ggtgtctaga tttctaatga agaatcatga
      tacagtttgg attaagtatc
4501  ttggactggt tttaaacagt gctttgtacc ggatctgctg
      aagcatctgt ccagctggta
4561  tcctgtgaaa gtttgttatt ttctgagtag acattcttat
      agagtattgt ctttaaaatc
4621  agattgtctc ttctatattg aaagcatttt tatgttttct
      aatttaaaaa ttaatatttt
4681  cttatagata ttgtgcaata aagctgaagt agaatgtgtg
      gttttgcaa atgctttaac
4741  agctgataaa aattttacat ttgtaaaatt aatatattgt
      actggtacaa aatagtttta
4801  aattatattt taaaaagctt ccaa
```

The polypeptide sequence of a HAT protein, human GCN5L, is depicted in SEQ ID NO: 5. The nucleotide sequence of human GCN5L is shown in SEQ ID NO: 6. Sequence information related to GCN5L is accessible in public databases by GenBank Accession numbers NM_021078 (for mRNA) and NP_066564.2 (for protein). GCN5L is also known as KAT2A (K(lysine) acetyltransferase 2A). KAT2A, or GCN5, is a histone acetyltransferase (HAT) that functions primarily as a transcriptional activator. It also functions as a repressor of NF-kappa-B by promoting ubiquitination of the NF-kappa-B subunit RELA in a HAT-independent manner (Mao et al., Genes Dev. 2009 Apr. 1; 23(7):849-61; each herein incorporated by reference in its entirety).

SEQ ID NO: 5 is the human wild type amino acid sequence corresponding to the HAT protein, the GCN5L enzyme (residues 1-837):

```
  1  MAEPSQAPTP APAAQPRPLQ SPAPAPTPTP APSPASAPIP
     TPTPAPAPAP AAAPAGSTGT
 61  GGPGVGSGGA GSGGDPARPG LSQQQRASQR KAQVRGLPRA
     KKLEKLGVFS ACKANETCKC
121  NGWKNPKPPT APRMDLQQPA ANLSELCRSC EHPLADHVSH
     LENVSEDEIN RLLGMVVDVE
181  NLFMSVHKEE DTDTKQVYFY LFKLLRKCIL QMTRPVVEGS
     LGSPPFEKPN IEQGVLNFVQ
```

```
241  YKFSHLAPRE RQTMFELSKM FLLCLNYWKL ETPAQFRQRS
     QAEDVATYKV NYTRWLCYCH
301  VPQSCDSLPR YETTHVFGRS LLRSIFTVTR RQLLEKFRVE
     KDKLVPEKRT LILTHFPKFL
361  SMLEEEIYGA NSPIWESGFT MPPSEGTQLV
     PRPASVSAAV VPSTPIFSPS MGGGSNSSLS
421  LDSAGAEPMP GEKRTLPENL TLEDAKRLRV MGDIPMELVN
     EVMLTITDPA AMLGPETSLL
481  SANAARDETA RLEERRGIIE FHVIGNSLTP KANRRVLLWL
     VGLQNVFSHQ LPRMPKEYIA
541  RLVFDPKHKT LALIKDGRVI GGICFRMFPT QGFTEIVFCA
     VTSNEQVKGY GTHLMNHLKE
601  YHIKHNILYF LTYADEYAIG YFKKQGFSKD IKVPKSRYLG
     YIKDYEGATL MECELNPRIP
661  YTELSHIIKK QKEIIKKLIE RKQAQIRKVY PGLSCFKEGV
     RQIPVESVPG IRETGWKPLG
721  KEKGKELKDP DQLYTTLKNL LAQIKSHPSA WPFMEPVKKS
     EAPDYYEVIR FPIDLKTMTE
781  RLRSRYYVTR KLFVADLQRV IANCREYNPP DSEYCRCASA
     LEKFFYFKLK EGGLIDK
```

SEQ ID NO: 6 is the human wild type nucleotide sequence corresponding to HAT protein, the GCN5L enzyme (residues 1-3127), wherein the underscored ATG denotes the beginning of the open reading frame:

```
   1  ggttgcccat gcggccctag ggctgggagc gcggcgccgc
      tctccgctgc ggggaggcc
  61  atggcggaac cttcccaggc cccgaccccg gccccggctg
      cgcagcccg gccccttcag
 121  tccccagccc ctgccccaac tccgactcct gcacccagcc
      cggcttcagc cccgattccg
 181  actcccaccc cggcaccagc ccctgcccca gctgcagccc
      cagccggcag cacagggact
 241  gggggccccg gggtaggaag tggggggggcc gggagcgggg
      gggatccggc tcgacctggc
 301  ctgagccagc agcagcgcgc cagtcagagg aaggcgcaag
      tccggggct gccgcgcgcc
 361  aagaagcttg agaagctagg ggtcttctcg gcttgcaagg
      ccaatgaaac ctgtaagtgt
 421  aatggctgga aaaaccccaa gccccccact gcaccccgca
      tggatctgca gcagccagct
 481  gccaacctga gtgagctgtg ccgcagttgt gagcacccct
      tggctgacca cgtatcccac
 541  ttggagaatg tgtcagagga tgagataaac cgactgctgg
      ggatggtggt ggatgtggag
 601  aatctcttca tgtctgttca aaggaagag gacacagaca
      ccaagcaggt ctatttctac
 661  ctcttcaagc tactgcggaa atgcatcctg cagatgaccc
      ggcctgtggt ggagggtcc
 721  ctgggcagcc tccatttga gaaacctaat attgagcagg
      gtgtgctgaa ctttgtgcag
 781  tacaagttta gtcacctggc tccccgggag cggcagacga
      tgttcgagct ctcaaagatg
 841  ttcttgctct gccttaacta ctggaagctt gagacacctg
      cccagtttcg gcagaggtct
 901  caggctgagg acgtggctac ctacaaggtc aattacacca
      gatggctctg ttactgccac
 961  gtgccccaga gctgtgatag cctccccgc tacgaaacca
      ctcatgtctt gggcgaagc
1021  cttctccggt ccattttcac cgttacccgc cggcagctgc
      tggaaaagtt ccgagtggag
1081  aaggacaaat tggtgcccga agaggacc ctcatcctca
      ctcacttccc caaattcctg
1141  tccatgctgg aggaggagat ctatgggca aactctccaa
      tctgggagtc aggcttcacc
1201  atgccaccct cagaggggac acagctggtt ccccggccag
      cttcagtcag tgcagcggtt
1261  gttcccagca ccccatctt cagccccagc atgggtgggg
      gcagcaacag ctccctgagt
1321  ctggattctg caggggccga gcctatgcca ggcgagaaga
      ggacgctccc agagaacctg
1381  accctggagg atgccaagcg gctccgtgtg atgggtgaca
      tccccatgga gctggtcaat
1441  gaggtcatgc tgaccatcac tgaccctgct gccatgctgg
      ggcctgagac gagcctgctt
1501  tcggccaatg cggcccggga tgagacagcc cgcctggagg
      agcgccgcgg catcatcgag
1561  ttccatgtca tcggcaactc actgacgccc aaggccaacc
      ggcgggtgtt gctgtggctc
1621  gtggggctga gaatgtctt tcccaccag ctgccgcgca
      tgcctaagga gtatatcgcc
```

```
1681  cgcctcgtct ttgacccgaa gcacaagact ctggccttga
      tcaaggatgg gcgggtcatc
1741  ggtggcatct gcttccgcat gtttcccacc cagggcttca
      cggagattgt cttctgtgct
1801  gtcacctcga atgagcaggt caagggttat gggacccacc
      tgatgaacca cctgaaggag
1861  tatcacatca agcacaacat tctctacttc ctcacctacg
      ccgacgagta cgccatcggc
1921  tacttcaaaa agcagggttt ctccaaggac atcaaggtgc
      ccaagagccg ctacctgggc
1981  tacatcaagg actacgaggg agcgacgctg atggagtgtg
      agctgaatcc ccgcatcccc
2041  tacacggagc tgtcccacat catcaagaag cagaaagaga
      tcatcaagaa gctgattgag
2101  cgcaaacagg cccagatccg caaggtctac ccggggctca
      gctgcttcaa ggagggcgtg
2161  aggcagatcc ctgtggagag cgttcctggc attcgagaga
      caggctggaa gccattgggg
2221  aaggagaagg ggaaggagct gaaggacccc gaccagctct
      acacaaccct caaaaacctg
2281  ctggcccaaa tcaagtctca ccccagtgcc tggcccttca
      tggagcctgt gaagaagtcg
2341  gaggcccctg actactacga ggtcatccgc ttccccattg
      acctgaagac catgactgag
2401  cggctgcgaa gccgctacta cgtgacccgg aagctctttg
      tggccgacct gcagcgggtc
2461  atcgccaact gtcgcgagta caaccccccg gacagcgagt
      actgccgctg tgccagcgcc
2521  ctggagaagt tcttctactt caagctcaag gagggaggcc
      tcattgacaa gtaggcccat
2581  ctttgggccg cagccctgac ctggaatgtc tccacctcgg
      attctgatct gatccttagg
2641  gggtgccctg gcccacgga cccgactcag cttgagacac
      tccagccaag ggtcctccgg
2701  acccgatcct gcagctcttt ctggaccttc aggcacccc
      aagcgtgcag ctctgtccca
2761  gccttcactg tgtgtgagag gtctcctggg ttggggccca
      gcccctctag agtagctggt
2821  ggccagggat gaaccttgcc cagccgtggt ggcccccagg
      cctggtcccc aagagctttg
2881  gaggcttgga ttcctgggcc tggcccaggt ggctgtttcc
      ctgaggacca gaactgctca
2941  ttttagcttg agtgatggct tcaggggttg gaagttcagc
      ccaaactgaa gggggccatg
3001  ccttgtccag cactgttctg tcagtctccc ccaggggtgg
      ggggtatggg gaccattcat
3061  tccctggcat taatcccta gagggaataa taaagctttt
      tatttctctg tgaaaaaaaa
3121  aaaaaaa
```

Knowledge of the primary sequence of a molecule of interest, such as a HAT polypeptide, and the similarity of that sequence with other proteins of the same histone acetyltransferase family (such as the GNAT family, the MYST family or the GCN5 family [see Lee and Owrkman (2007) *Nat Rev Mol Cell Biol.*, 8(4):284-95, Marmorstein (2001) *J Molec Biol.* 311: 433-444; and Kimura et al., (2005) *J Biochem.* 138(6): 647-662; each herein incorporated by reference in its entirety]), can provide information as to the inhibitors or antagonists of the protein of interest. Identification and screening antagonists can be further facilitated by determining structural features of the protein, e.g., using X-ray crystallography, neutron diffraction, nuclear magnetic resonance spectrometry, and other techniques for structure determination. These techniques may provide for rational approaches to the design or identification of antagonists, in addition to protein agonists.

A HAT Activator compound can be a compound that increases the activity and/or expression of a HAT molecule (e.g., GCN5, GCN5L, PCAF, or HAT1) in vivo and/or in vitro. HAT Activator compounds can be compounds that exert their effect on the activity of a HAT protein via the expression, via post-translational modifications, or by other means. In some embodiments, a HAT Activator compound can increase HAT protein or mRNA expression, or acetyltransferase activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

In some embodiments, the methods comprise administering to the subject an effective amount of a composition comprising compound (I). In some embodiments, the subject does not exhibit abnormally elevated amyloid beta plaques, elevated Tau protein levels, accumulations of alpha-synuclein, accumulations of lipofuscin, or accumulation of cleaved TARDBP (TDB-43) levels, or any combination thereof. In some embodiments, the subject is not afflicted with Alzheimer's disease, Lewy body dementia, inclusion body myositis, Huntington's Disease, Parkinson's Disease, or cerebral amyloid angiopathy. In some embodiments, the subject is not afflicted with cancer.

In some embodiments, the method of treatment comprises the steps of: i) identifying a subject in need of such treatment; (ii) providing compound (I), or a pharmaceutically acceptable salt thereof; and (iii) administering said compound in a therapeutically effective amount to a subject in need of such treatment.

In some embodiments, the method of treatment comprises the steps of: i) identifying a subject in need of such treatment; (ii) providing a composition comprising compound (I), or a pharmaceutically acceptable salt thereof; and (iii) administering said composition in a therapeutically effective amount to a subject in need of such treatment.

In some embodiments, the methods comprise administering to the subject an effective amount of compound (I), or a pharmaceutically acceptable salt thereof, or a composition comprising compound (I), or a pharmaceutically acceptable salt thereof, and a pharmaceutically acceptable carrier. The pharmaceutically acceptable carriers are well-known to those skilled in the art, and include, for example, adjuvants, diluents, excipients, fillers, lubricants and vehicles. Often, the pharmaceutically acceptable carrier is chemically inert toward the active compounds and is non-toxic under the conditions of use. Examples of pharmaceutically acceptable carriers may include, for example, water or saline solution, polymers such as polyethylene glycol, carbohydrates and derivatives thereof, oils, fatty acids, or alcohols.

In one aspect, the invention is directed to the use of compound (I), or a pharmaceutically acceptable salt thereof, in preparation of a medicament for enhancing learning or memory in a subject.

In one aspect, the invention is directed to the use of compound (I), or a pharmaceutically acceptable salt thereof, in preparation of a medicament for increasing histone acetylation in a subject.

In one aspect, the invention is directed to the use of compound (I), or a pharmaceutically acceptable salt thereof, in preparation of a medicament for improving memory retention in a subject.

In one aspect, the invention is directed to the use of compound (I), or a pharmaceutically acceptable salt thereof, in preparation of a medicament for treating memory loss or a learning disability in a subject.

In some embodiments, compound (I) is formulated into pharmaceutical compositions for administration to subjects in a biologically compatible form suitable for administration in vivo. According to some embodiments, the present invention provides a pharmaceutical composition comprising compound (I) in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as absorption delaying agents, analgesics, antibacterials, antifungals, buffers, binders, coatings, disintegrants, diluents, dispersants, emulsifiers, excipients, extenders, glidants, solubilizers, solvents, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, When administered to a subject, compound (I) and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present invention are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compound and/or compositions of the present invention are administered to a human or animal subject by known procedures including oral administration, intraperitoneal, parenteral (e.g., intravenous), intradermal, subcutaneous, intranasal, transdermal, topical, transmucosal, rectal, sublingual or buccal administration. In some embodiments, compound (I) or a composition comprising compound (I) is administered orally. In some embodiments, compound (I) or a composition comprising compound (I) is administered intraperitoneally.

For oral administration, a formulation of compound (I) or compositions thereof may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, for example, sweetening agents such as fructose, aspartame or saccharin; flavoring agents such as peppermint, oil of wintergreen, or cherry; coloring agents; and preservative agents, to provide a pharmaceutically palatable preparation.

The compositions may further comprise one or more sterile diluents, such as water, saline solutions, fixed oils, polyalkylene glycols, polyoxyalkylene glycols, glycerine, or other solvents; antibacterial agents such as benzyl alcohol or methyl parabens, antioxidants such as ascorbic acid, citric acid or sodium bisulfite, chelating agents such as EDTA, buffers such as acetate, citrate, phosphate and the like, tonicity adjusters such as sodium chloride or dextrose, pH adjusters such as weak acids or bases, etc.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition is preferably sterile and should be fluid to the extent that easy syringability exists. It is preferably stable under the conditions of manufacture and storage and is preferably preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating compound (I) or a composition thereof in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The parenteral preparation can be enclosed in ampoules, disposable syringes or multiple dose vials made of glass or plastic.

In accordance with the methods of the present invention, in some embodiments the compounds and/or compositions of the invention are administered to the subject in a therapeutically effective amount to enhance or increase memory or cognition in the subject. This amount is readily determined by the skilled artisan, based upon known procedures, including analysis of titration curves established in vivo and methods and assays disclosed herein.

The dosage administered can be a therapeutically effective amount of the composition sufficient to result in memory or cognitive enhancement, increasing learning, or reducing memory loss in a subject.

In some embodiments, the methods comprise administration of a therapeutically effective dosage of compound (I). In some embodiments, the therapeutically effective dosage is at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In some embodiments, the methods comprise administration over the course of several years or decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each patient's circumstances. In some embodiments of the invention, suitable dose ranges for oral administration of compound (I) are generally about 5 mg/day to about 1000 mg/day. In some embodiments, the oral dose of compound (I) is about 5 mg/day to about 800 mg/day. In some embodiments, the oral dose of compound (I) is about 5 mg/day to about 500 mg/day. In some embodiments, the oral dose of compound (I) is about 5 mg/day to about 250 mg/day. In some embodiments, the oral dose of compound (I) is about 5 mg/day to about 100 mg/day. In some embodiments, the oral dose of compound (I) is about 5 mg/day to about 50 mg/day. In some embodiments, the oral dose of compound (I) is about 5 mg/day. In some embodiments, the oral dose of compound (I) is about 10 mg/day. In some embodiments, the oral dose of compound (I) is about 20 mg/day. In some embodiments, the oral dose of compound (I) is about 50 mg/day. In some embodiments, the oral dose of compound (I) is about 100 mg/day. In some embodiments, the oral dose of compound (I) is about 250 mg/day. In some embodiments, the oral dose of compound (I) is about 500 mg/day. In some embodiments, the oral dose of compound (I) is about 750 mg/day. In some embodiments, the oral dose of compound (I) is about 1000 mg/day.

In some embodiments of the invention, suitable dose ranges for i.p. administration of compound (I) are generally about 5 mg/day to about 1000 mg/day. In some embodiments, the i.p. dose of compound (I) is about 5 mg/day to about 800 mg/day. In some embodiments, the i.p. dose of compound (I) is about 5 mg/day to about 500 mg/day. In some embodiments, the i.p. dose of compound (I) is about 5 mg/day to about 250 mg/day. In some embodiments, the i.p. dose of compound (I) is about 5 mg/day to about 100 mg/day. In some embodiments, the i.p. dose of compound (I) is about 5 mg/day to about 50 mg/day. In some embodiments, the i.p. dose of compound (I) is about 5 mg/day. In some embodiments, the i.p. dose of compound (I) is about 10 mg/day. In some embodiments, the i.p. dose of compound (I) is about 20 mg/day. In some embodiments, the i.p. dose of compound (I) is about 50 mg/day. In some embodiments, the i.p. dose of compound (I) is about 100 mg/day. In some embodiments, the i.p. dose of compound (I) is about 250 mg/day. In some embodiments, the i.p. dose of compound (I) is about 500 mg/day. In some embodiments, the i.p. dose of compound (I) is about 750 mg/day. In some embodiments, the i.p. dose of compound (I) is about 1000 mg/day.

Any of the therapeutic applications described herein can be applied to any subject in need of such therapy, including, for example, a mammal such as a mouse, rat, dog, a cat, a cow, a horse, a rabbit, a monkey, a pig, a sheep, a goat, or a human.

It will recognized that one or more features of any embodiments disclosed herein may be combined and/or rearranged within the scope of the invention to produce further embodiments that are also within the scope of the invention.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Synthesis of Compound 1

Scheme 1: Synthesis of Compound 1.

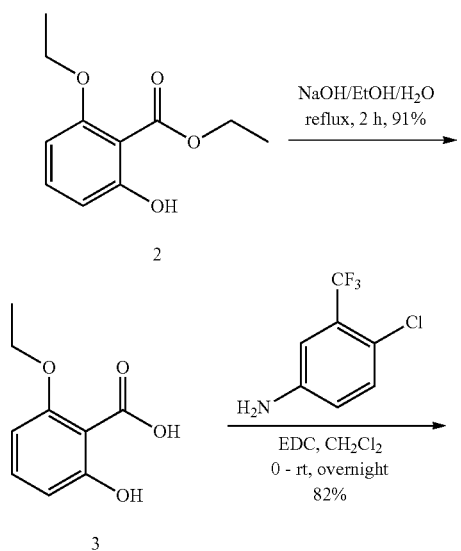

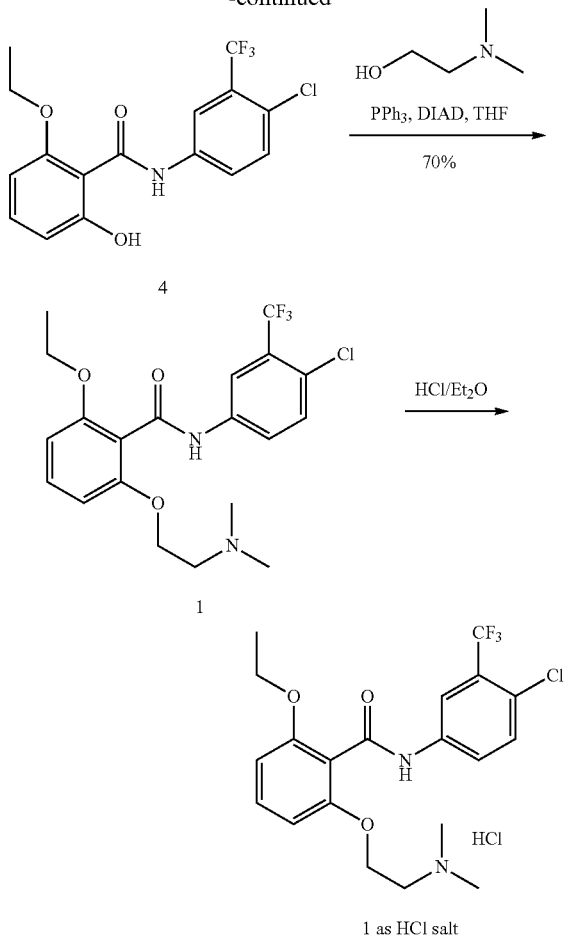

HAT Activator compound, compound 1 (I) was prepared according to Scheme 1. A solution of commercially available ethyl 6-ethoxy-2-hydroxybenzoate (2.10 g, 10.0 mmol) in EtOH and NaOH 1N (10 mL, 1:1) was heated to reflux for 2 h. The solution was acidified by adding HCl 1N and the resulting precipitate was diluted with CH$_2$Cl$_2$ (50 mL) and washed with HCl 1N (3×50 mL). The organic layer was dried under Na$_2$SO$_4$, filtered and evaporated under reduced pressure. A white solid was obtained as the desired product 3 (1.65 g, 91%).

EDC (2.19 mL, 12.35 mmol) was added dropwise to a solution of 3 (1.5 g, 8.23 mmol) and 3-chloro-4-(trifluoromethyl)aniline (1.61 g, 8.23 mmol) in CH$_2$Cl$_2$ (15 mL) at 0° C. The reaction was stirred at room temperature overnight. The solvent was evaporated under reduced pressure and the final product 4 (2.42 g, 82%) was isolated by precipitation from MeOH as a white needle-like solid.

To a solution of 4 (170 mg, 0.47 mmol), 2-(dimethylamino)ethanol (54 mg, 0.6 mmol), and PPh$_3$ (157 mg, 0.6 mmol) in THF (5 mL) DIAD (121 mg, 0.6 mmol) was added dropwise. The reaction was stirred for 24 h at room temperature. The solvent was removed under reduced pressure, and the residue was dissolved in AcOEt (30 mL). The organic layer was washed with water (3×30 mL), dried under Na$_2$SO$_4$, filtered, and concentrated to give a yellow oil, which was purified by flash chromatography (AcOEt: MeOH 9:1) affording compound 1 (135 mg, 70%) as a colorless oil. $^1$H NMR (CDCl$_3$, 300 MHz) δ 8.65 (s, 1H), 7.98 (d, 1H, J=7.8 Hz), 7.79 (d, 1H, J=1.5 Hz), 7.46 (d, 1H, J=8.7 Hz), 7.29 (t, 1H, J=8.4 Hz), 6.60 (dd, 2H, J$_1$=1.8, J$_2$=8.4 Hz), 4.20 (t, 2H, J=5.1 Hz), 4.10 (q, 2H, J=6.9 Hz), 2.65 (t, 2H, J=5.4 Hz), 2.25 (s, 6H), 1.40 (t, 3H, J=7.2 Hz); Ms ESI (m/z) 431 (M+1)$^+$. Compound 1 was treated with HCl 2M solution in ethyl ether and the white salt of 1 was collected by filtration.

Example 2

HAT Activator Compound Characteristics

Figure 2:
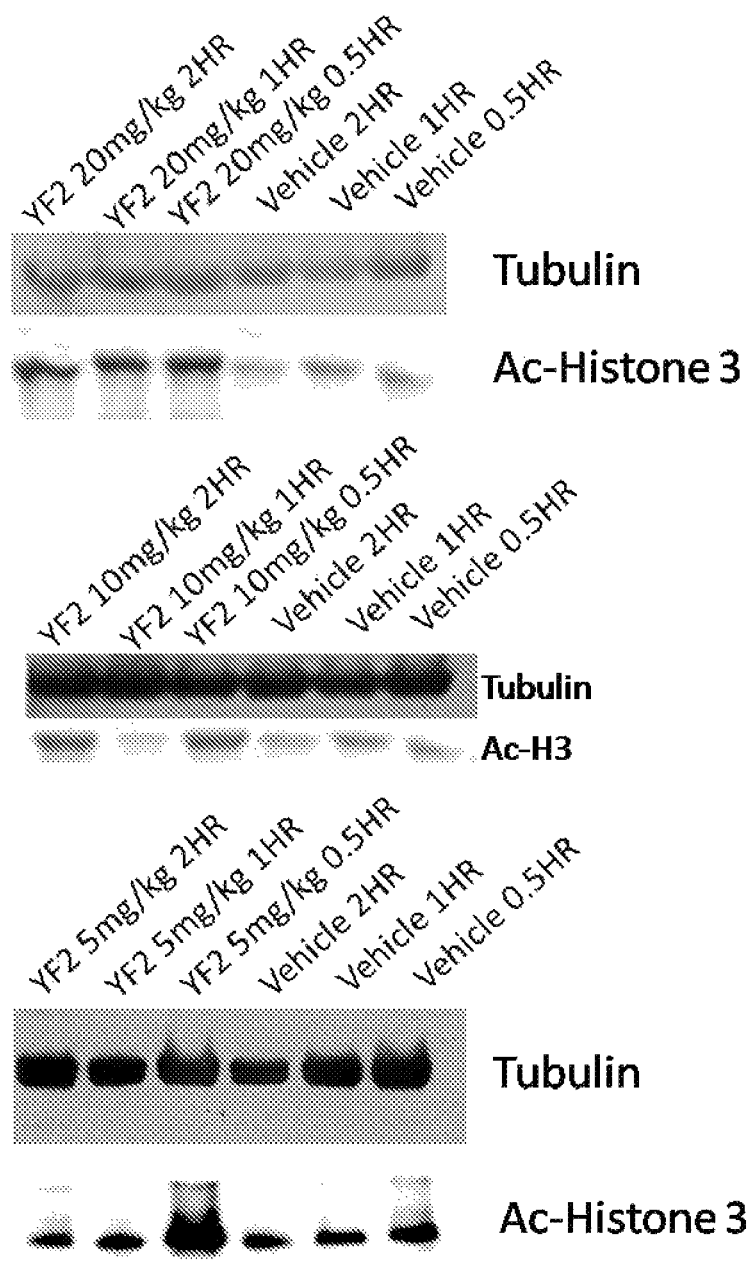
FIG. 2 is a photograph of a western blot showing acetylation levels of H3 in the hippocampus. Mice were administered with YF2 (Compound 1) (i.p. dissolved in saline) at 5 mg/kg, 10 mg/kg, or 20 mg/kg.

The preparation of compound 1 was without a column and 2 phases were visible: clear and oily. Compound 1 (50 mg/kg, i.p.) was subsequently administered to mice. The des-ethoxy analog of compound 1, MOM, was also administered via cannula (100 µg/µL per side). Two and four hrs after its administration, the mice were sacrificed and hippocampi were extracted. Interestingly, while MOM did not cross the BBB, YF2 (compound 1) was able to cross the BBB, penetrate the cells and increase ACH3 (lane 1 vs. lanes 9, 10) (FIG. 1). Given that the compound was not 100% clean and needed to be further purified/verified, more compound 1 was synthesized and purified. Purity was verified through Nuclear Magnetic Resonance (NMR) spectroscopy. Mice were administered with compound 1 (i.p. dissolved in saline) at 5, 10, 20 mg/Kg. Hippocampus extraction was made at 3 different time points (0.5, 1 and 2 hrs post treatment). A western blotting for ACH3 was then performed. Except for the 1 hr-10 mg/kg administration of YF2, YF2 dramatically increased ACH3 levels (FIG. 2), indicating that YF2 (compound 1) crosses the BBB and the cell membrane.

Example 3

Compound 1 Increases Histone Acetylation by HAT Activation, not HDAC Inhibition

HDAC inhibition causes an increase in histone acetylation. The inventors examined whether histone acetylation occurred via HDAC inhibition. The summary of the results is depicted in Table 1. The mean IC$_{50}$ values of the compounds (compound 1 and SAHA) are summarized in Table 1.

TABLE 1

Inhibitory Effects of the Compounds on HDAC Activities

| | IC$_{50}$ (nM) or % Inhibition | |
|---|---|---|
| HDACs | 1 | SAHA |
| HDAC1 | >200 µM | 31 |
| HDAC3/NCOR2 | >200 µM | 38 |
| HDAC5FL | >200 µM | >10 µM |
| HDAC6 | >200 µM | 30 |
| HADC7 | >200 µM | >10 µM |
| HDAC8 | >200 µM | 2,236 |
| HDAC10 | >200 µM | 65 |
| HDAC11 | >200 µM | >10 µM |
| Sirtuin 1 | >200 µM | >10 µM |
| Sirtuin 2 | >200 µM | >10 µM |

The experiments were done blind, and the studies show that compound 1 has no HDAC inhibition properties. Compound 1 does not inhibit HDACs.

Materials and Methods
Materials:
HDAC Assay Buffer (BPS catalog number 50031)
HDAC Assay Developer (BPS catalog number 50030)
HDAC Substrate 1 (BPS number 50032)
HDAC Substrate 3 (BPS number 50037)
HDAC Class 2a Substrate 1 (BPS number 50040)
SAHA (Cayman Chemical, Ann Arbor, Mich., Catalog number 10009929)

TABLE 2

Compounds used in the studies

| Compound I.D. | Compound Supplied | Stock Conc. | Dissolving Solvent | Test Range (nM) | Intermediate Dilution |
|---|---|---|---|---|---|
| 1* | Solution | 10 mM | DMSO | 3-200,000 | 10% DMSO in HDAC Assay Buffer |
| SAHA | Powder | 10 mM | DMSO | 0.3-10,000 | 10% DMSO in HDAC Assay Buffer |

*Compound 1 is cloudy at 2 mM in 10% DMSO (The highest test point).
**SAHA, and HDACi, is a positive control for HDACs.

Experimental Conditions

TABLE 3

Enzymes and Substrates

| Assay | Catalog # | Enzyme Used (ng)/Reaction | Substrate |
|---|---|---|---|
| HDAC1 | 50051 | 1.5 | 10 μM of 50037 |
| HADC3/NCOR2 | 50003 | 1.33 | 10 μM of 50037 |
| HDAC5FL | 50045 | 1.25 | 2 μM of 50040 |
| HDAC6 | 50006 | 10 | 10 μM of 50037 |
| HDAC7 | 50007 | 0.3 | 2 μM of 50040 |
| HDAC8 | 50008 | 20 | 2 μM of 50040 |
| HDAC10 | 50010 | 1,300 | 10 μM of 50037 |
| HADC11 | 50011 | 400 | 2 μM of 50040 |
| Sirtuin 1 | 50012 | 400 | 10 μM of 50032 |
| Sirtuin 2 | 50013 | 5,600 | 10 μM of 50032 |

Assay Conditions. A series of dilution of the test compounds were prepared with 10% DMSO in assay buffer and 5 μl of the dilution was added to a 50 μl reaction so that the final concentration of DMSO is 1% in all of reactions. All of the enzymatic reactions were conducted in duplicate at 37° C. for 30 minutes except of HDAC11 at room temperature for 3 hours. The 50 μl reaction mixture contains HDAC assay buffer, 5 μg BSA, an HDAC substrate, an HDAC enzyme and a test compound. After enzymatic reactions, 50 μl of HDAC Developer was added to each well and the plate was incubated at room temperature for an additional 20 minutes. Fluorescence intensity was measured at an excitation of 360 nm and an emission of 460 nm using a Tecan Infinite M1000 microplate reader.

Data Analysis. HDAC activity assays were performed in duplicates at each concentration. The fluorescent intensity data were analyzed using the computer software, Graphpad Prism. In the absence of the compound, the fluorescent intensity ($F_t$) in each data set was defined as 100% activity. In the absence of HDAC, the fluorescent intensity ($F_b$) in each data set was defined as 0% activity. Compound 1 has fluorescence at assay condition; therefore the fluorescent intensity at different concentration of compound 1 was defined as background (Fb). The percent activity in the presence of each compound was calculated according to the following equation: % activity=$(F-F_b)/(F_t-F_b)$, where F=the fluorescent intensity in the presence of the compound.

The values of % activity versus a series of compound concentrations were then plotted using non-linear regression analysis of Sigmoidal dose-response curve generated with the equation $Y=B+(T-B)/1+10^{(LogEC50-X) \times Hill\ Slope}$, where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity.

Results of Effect of Compound 1 on HDAC Inhibition

TABLE 4

HDAC1 Assay - Data for the Effect of Compound 1 on HDAC1 Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 17721 | 17257 | 796 | 803 | 101.39 | 98.61 |
| 0.5 | 17287 | 17200 | 796 | 798 | 98.80 | 98.28 |
| 1.0 | 17083 | 17178 | 788 | 786 | 97.64 | 98.21 |
| 1.5 | 16949 | 17020 | 830 | 784 | 96.72 | 97.14 |
| 2.0 | 16879 | 16826 | 796 | 779 | 96.42 | 96.10 |
| 2.5 | 16792 | 17072 | 827 | 775 | 95.81 | 97.49 |
| 3.0 | 16943 | 16784 | 829 | 802 | 96.63 | 95.68 |
| 3.5 | 16387 | 17135 | 866 | 827 | 93.12 | 97.60 |
| 4.0 | 16140 | 16336 | 920 | 868 | 91.35 | 92.53 |
| 4.5 | 16432 | 16128 | 1117 | 1035 | 92.01 | 90.19 |
| 5.3 | 24780 | 24451 | 14884 | 13403 | 63.73 | 61.76 |

Figure 3:
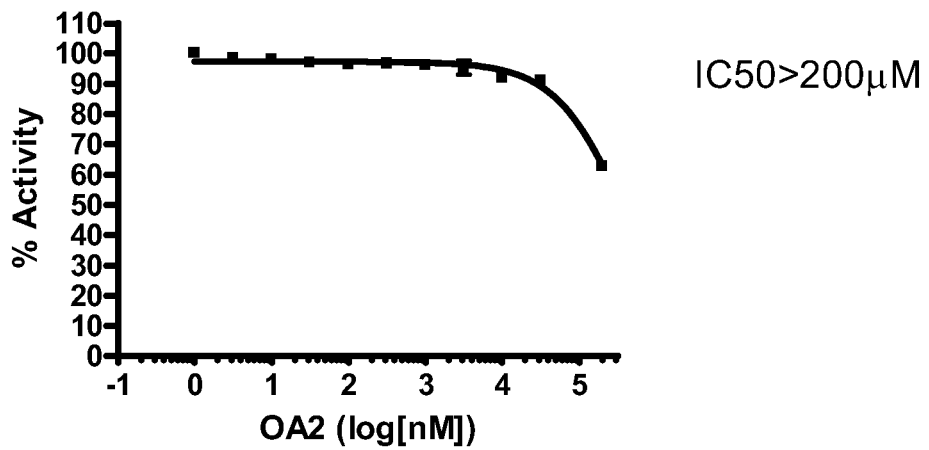
FIG. 3 is a graph showing the effect of OA2 (Compound 1) on HDAC1 activity.

FIG. 3 corresponds to the results shown in Table 4.

TABLE 5

HDAC3/NCOR2 Assay - Data for the Effect of Compound 1 on HDAC3/NCOR2 Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 10787 | 10452 | 805 | 828 | 101.71 | 98.29 |
| 0.5 | 10928 | 9694 | 813 | 976 | 102.35 | 89.76 |
| 1.0 | 10423 | 10379 | 812 | 818 | 98.01 | 97.56 |
| 1.5 | 10752 | 10231 | 813 | 803 | 101.44 | 96.12 |
| 2.0 | 10827 | 10078 | 809 | 798 | 102.25 | 94.61 |
| 2.5 | 10718 | 10173 | 818 | 803 | 101.07 | 95.51 |
| 3.0 | 10587 | 10073 | 831 | 811 | 99.62 | 94.38 |
| 3.5 | 10362 | 10080 | 854 | 824 | 97.14 | 94.27 |
| 4.0 | 11530 | 10216 | 927 | 898 | 108.31 | 94.90 |
| 4.5 | 9872 | 10001 | 1467 | 1091 | 87.66 | 88.97 |
| 5.3 | 20905 | 22163 | 13408 | 10875 | 89.40 | 102.23 |

Figure 4:
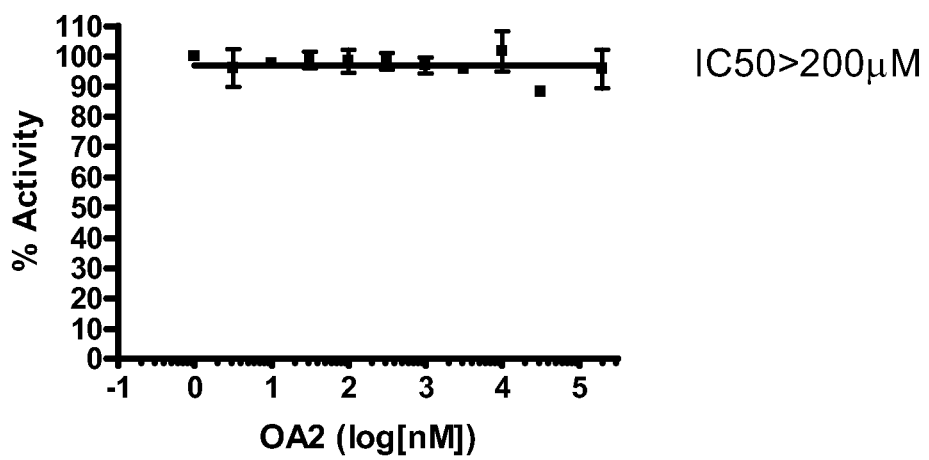
FIG. 4 is a graph showing the effect of OA2 (Compound 1) on HDAC3/NCOR2 activity.

FIG. 4 corresponds to the results shown in Table 5.

TABLE 6

HDAC5FL Assay - Data for the Effect of Compound 1 on HDAC5FL Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 4492 | 4892 | 345 | 348 | 95.40 | 104.60 |
| 0.5 | 4686 | 4386 | 355 | 343 | 99.80 | 92.90 |
| 1.0 | 4802 | 4581 | 341 | 347 | 102.59 | 97.50 |

TABLE 6-continued

HDAC5FL Assay - Data for the Effect of Compound 1 on HDAC5FL Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| 1.5 | 4835 | 4874 | 359 | 342 | 103.20 | 104.10 |
| 2.0 | 5071 | 4991 | 344 | 356 | 108.64 | 106.80 |
| 2.5 | 5068 | 5006 | 344 | 354 | 108.60 | 107.17 |
| 3.0 | 4944 | 4685 | 342 | 354 | 105.76 | 99.80 |
| 3.5 | 4773 | 4686 | 353 | 389 | 101.30 | 99.30 |
| 4.0 | 4987 | 4983 | 449 | 407 | 104.91 | 104.82 |
| 4.5 | 4570 | 4514 | 451 | 398 | 95.40 | 94.11 |
| 5.3 | 9875 | 10983 | 7907 | 5878 | 68.63 | 94.13 |

Figure 5:
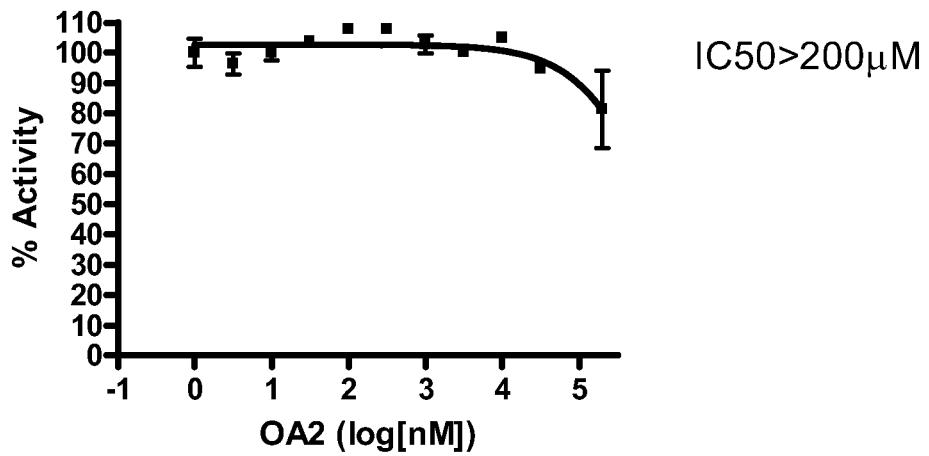
FIG. 5 is a graph showing the effect of OA2 (Compound 1) on HDAC5FL activity.

FIG. 5 corresponds to the results shown in Table 6.

TABLE 7

HDAC7 Assay - Data for the Effect of Compound 1 on HDAC7 Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 7528 | 7176 | 382 | 377 | 102.52 | 97.48 |
| 0.5 | 7578 | 7200 | 394 | 383 | 103.11 | 97.69 |
| 1.0 | 6756 | 6763 | 385 | 386 | 91.37 | 91.47 |
| 1.5 | 7471 | 7705 | 389 | 381 | 101.63 | 104.98 |
| 2.0 | 7679 | 7196 | 390 | 380 | 104.61 | 97.68 |
| 2.5 | 7071 | 7068 | 385 | 398 | 95.80 | 95.75 |
| 3.0 | 7083 | 7269 | 384 | 392 | 96.02 | 98.69 |
| 3.5 | 7453 | 6898 | 397 | 462 | 100.73 | 92.77 |
| 4.0 | 6801 | 7568 | 416 | 534 | 90.73 | 101.73 |
| 4.5 | 7238 | 7518 | 554 | 565 | 95.78 | 99.80 |
| 5.3 | 9692 | 9912 | 3002 | 2871 | 96.89 | 100.04 |

Figure 6:
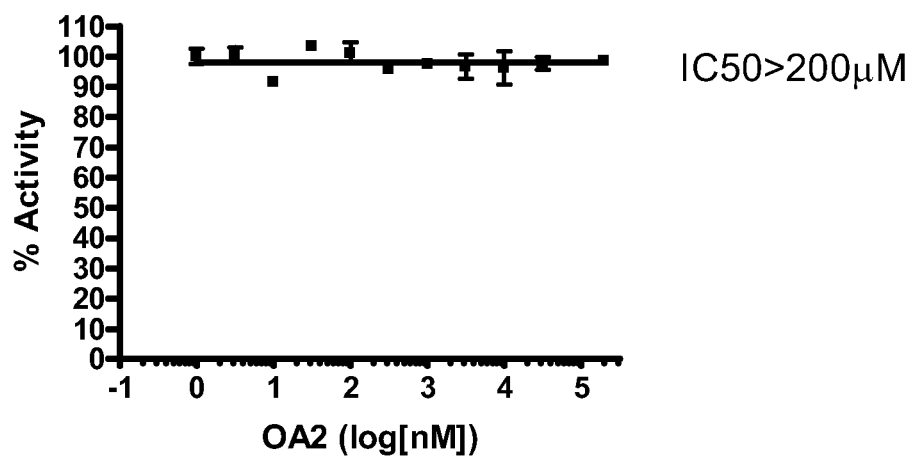
FIG. 6 is a graph showing the effect of OA2 (Compound 1) on HDAC7 activity.

FIG. 6 corresponds to the results shown in Table 7.

TABLE 8

HDAC8 Assay - Data for the Effect of Compound 1 on HDAC8 Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 3492 | 3483 | 346 | 346 | 100.14 | 99.86 |
| 0.5 | 3541 | 3581 | 339 | 342 | 101.88 | 103.15 |
| 1.0 | 3519 | 3391 | 349 | 342 | 101.02 | 96.94 |
| 1.5 | 3539 | 3456 | 336 | 331 | 102.04 | 99.40 |
| 2.0 | 3757 | 3425 | 338 | 340 | 108.80 | 98.23 |
| 2.5 | 3451 | 3428 | 335 | 341 | 99.09 | 98.36 |
| 3.0 | 3398 | 2995 | 337 | 347 | 97.28 | 84.45 |
| 3.5 | 3808 | 3407 | 346 | 366 | 109.88 | 97.12 |
| 4.0 | 3361 | 3365 | 433 | 374 | 94.14 | 94.27 |
| 4.5 | 3045 | 3090 | 375 | 364 | 85.17 | 86.60 |
| 5.3 | 6631 | 8117 | 4962 | 4635 | 58.33 | 105.63 |

Figure 7:
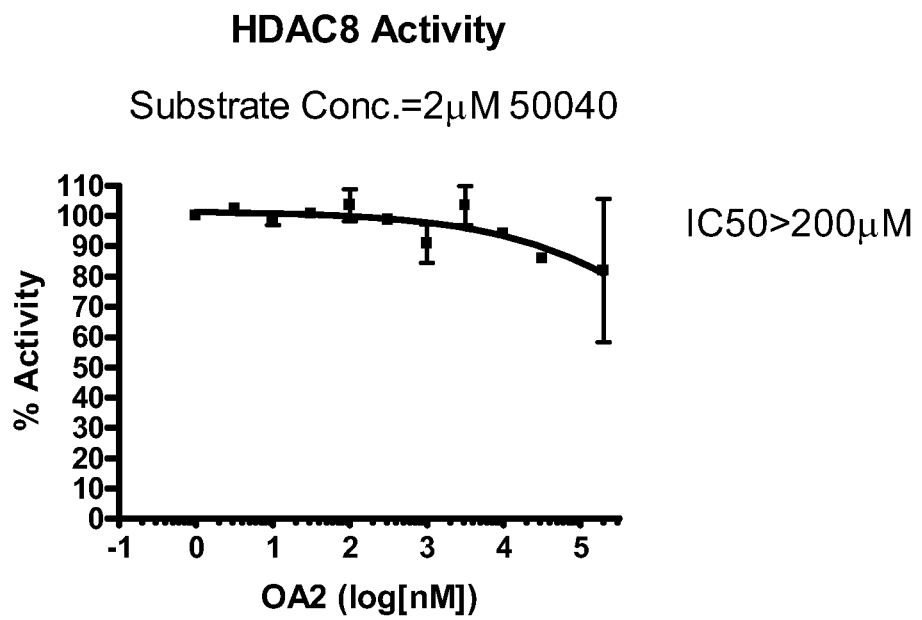
FIG. 7 is a graph showing the effect of OA2 (Compound 1) on HDAC8 activity.

FIG. 7 corresponds to the results shown in Table 8.

TABLE 9

HDAC10 Assay - Data for the Effect of Compound 1 on HDAC10 Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 11695 | 12141 | 497 | 507 | 98.05 | 101.95 |
| 0.5 | 10894 | 12032 | 492 | 501 | 91.08 | 101.05 |
| 1.0 | 12341 | 12402 | 497 | 492 | 103.77 | 104.31 |
| 1.5 | 12564 | 12368 | 525 | 500 | 105.57 | 103.85 |
| 2.0 | 12262 | 12573 | 500 | 497 | 103.04 | 105.77 |
| 2.5 | 12472 | 12556 | 500 | 493 | 104.90 | 105.64 |
| 3.0 | 11935 | 12471 | 530 | 521 | 99.94 | 104.64 |
| 3.5 | 11622 | 12684 | 501 | 607 | 96.95 | 106.25 |
| 4.0 | 11588 | 12318 | 597 | 547 | 96.50 | 102.89 |
| 4.5 | 11448 | 12305 | 623 | 495 | 95.38 | 102.89 |
| 5.3 | 25769 | 22285 | 12210 | 12714 | 116.56 | 86.05 |

Figure 8:
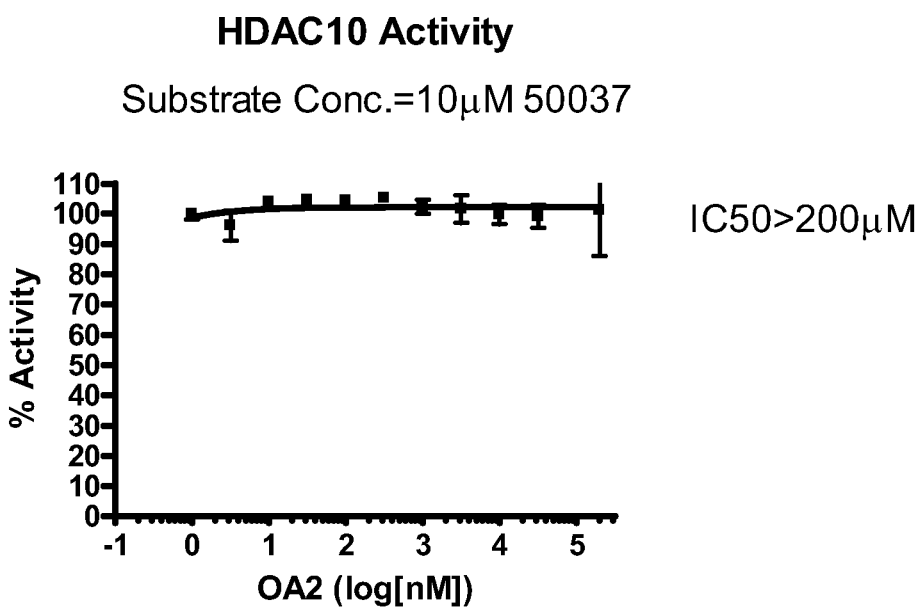
FIG. 8 is a graph showing the effect of OA2 (Compound 1) on HDAC10 activity.

FIG. 8 corresponds to the results shown in Table 9.

TABLE 10

HDAC11 Assay - Data for the Effect of Compound 1 on HDAC11 Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 2840 | 2860 | 426 | 406 | 99.59 | 100.41 |
| 0.5 | 2761 | 2530 | 411 | 423 | 96.30 | 86.81 |
| 1.0 | 2828 | 2898 | 425 | 415 | 98.93 | 101.81 |
| 1.5 | 2765 | 2851 | 411 | 406 | 96.82 | 100.35 |
| 2.0 | 2812 | 2864 | 408 | 409 | 98.75 | 100.88 |
| 2.5 | 2672 | 2655 | 412 | 408 | 92.93 | 92.24 |
| 3.0 | 2829 | 2806 | 417 | 424 | 98.95 | 98.01 |
| 3.5 | 2719 | 2712 | 427 | 463 | 93.43 | 93.14 |
| 4.0 | 2835 | 2860 | 467 | 524 | 96.12 | 97.14 |
| 4.5 | 3289 | 3064 | 699 | 617 | 108.09 | 98.85 |
| 5.3 | 6249 | 5842 | 2911 | 3158 | 132.07 | 115.35 |

Figure 9:
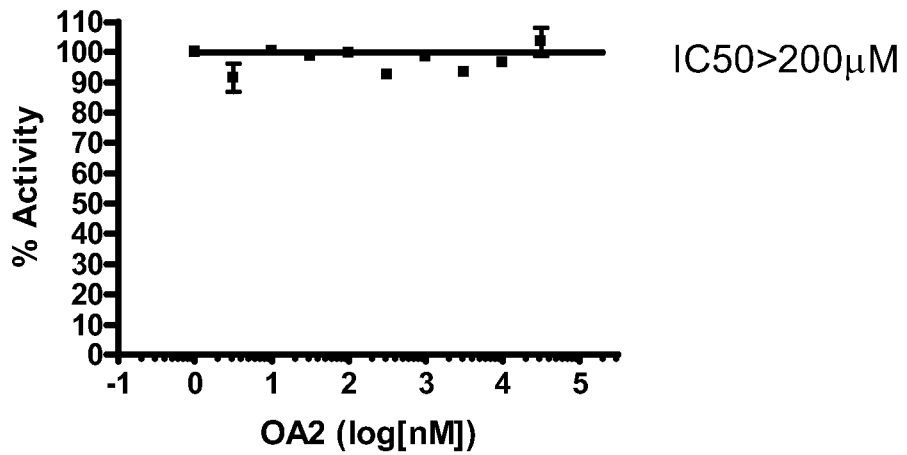
FIG. 9 is a graph showing the effect of OA2 (Compound 1) on HDAC11 activity.

FIG. 9 corresponds to the results shown in Table 10.

TABLE 11

Sirtuin 1 Assay - Data for the Effect of Compound 1 on Sirtuin 1 Activity

| Compound 1 | HDAC Activity (Fluorescence count) | | Background (Fluorescence count) | | % Activity | |
|---|---|---|---|---|---|---|
| (Log [nM]) | Repeat1 | Repeat2 | Repeat1 | Repeat2 | Repeat1 | Repeat2 |
| No CPD | 5823 | 5974 | 412 | 410 | 97.91 | 100.64 |
| 0.5 | 5627 | 5940 | 414 | 420 | 94.26 | 99.92 |
| 1.0 | 5240 | 5913 | 422 | 413 | 87.25 | 99.42 |
| 1.5 | 5980 | 5273 | 418 | 457 | 100.27 | 87.48 |
| 2.0 | 5827 | 5527 | 411 | 411 | 97.98 | 92.56 |
| 2.5 | 6028 | 5987 | 413 | 416 | 101.56 | 100.81 |
| 3.0 | 6454 | 5681 | 422 | 452 | 108.86 | 94.87 |
| 3.5 | 5782 | 5964 | 422 | 426 | 96.93 | 100.23 |
| 4.0 | 5786 | 5408 | 442 | 441 | 96.69 | 89.85 |

TABLE 11-continued

Sirtuin 1 Assay - Data for the Effect of Compound 1 on Sirtuin 1 Activity

| Compound 1 (Log [nM]) | HDAC Activity (Fluorescence count) | | Background (Fluorescence count) | | % Activity | |
|---|---|---|---|---|---|---|
| | Repeat1 | Repeat2 | Repeat1 | Repeat2 | Repeat1 | Repeat2 |
| 4.5 | 5976 | 5697 | 502 | 524 | 98.83 | 93.79 |
| 5.3 | 7483 | 7591 | 2022 | 1997 | 99.02 | 100.98 |

Figure 10:
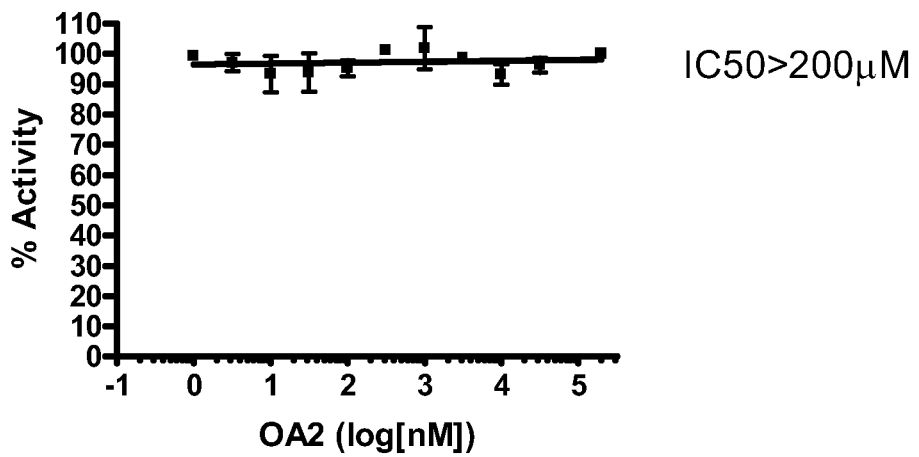
FIG. 10 is a graph showing the effect of OA2 (Compound 1) on Sirtuin1 activity.

FIG. 10 corresponds to the results shown in Table 11.

TABLE 12

Sirtuin 2 Assay - Data for the Effect of Compound 1 on Sirtuin 2 Activity

| Compound 1 (Log [nM]) | HDAC Activity (Fluorescence count) | | Background (Fluorescence count) | | % Activity | |
|---|---|---|---|---|---|---|
| | Repeat1 | Repeat2 | Repeat1 | Repeat2 | Repeat1 | Repeat2 |
| No CPD | 3910 | 3919 | 413 | 419 | 99.87 | 100.13 |
| 0.5 | 3835 | 3981 | 420 | 413 | 97.71 | 101.89 |
| 1.0 | 3780 | 3821 | 406 | 422 | 96.21 | 97.38 |
| 1.5 | 3858 | 3954 | 408 | 410 | 98.59 | 101.33 |
| 2.0 | 3712 | 3912 | 420 | 413 | 94.20 | 99.91 |
| 2.5 | 3729 | 3788 | 409 | 420 | 94.74 | 96.43 |
| 3.0 | 3714 | 3861 | 405 | 409 | 94.53 | 98.73 |
| 3.5 | 3806 | 3856 | 422 | 417 | 96.80 | 98.23 |
| 4.0 | 3844 | 3883 | 425 | 426 | 97.71 | 98.83 |
| 4.5 | 3717 | 3811 | 485 | 480 | 92.45 | 95.14 |
| 5.3 | 5686 | 5717 | 2225 | 2245 | 98.64 | 99.53 |

Figure 11:
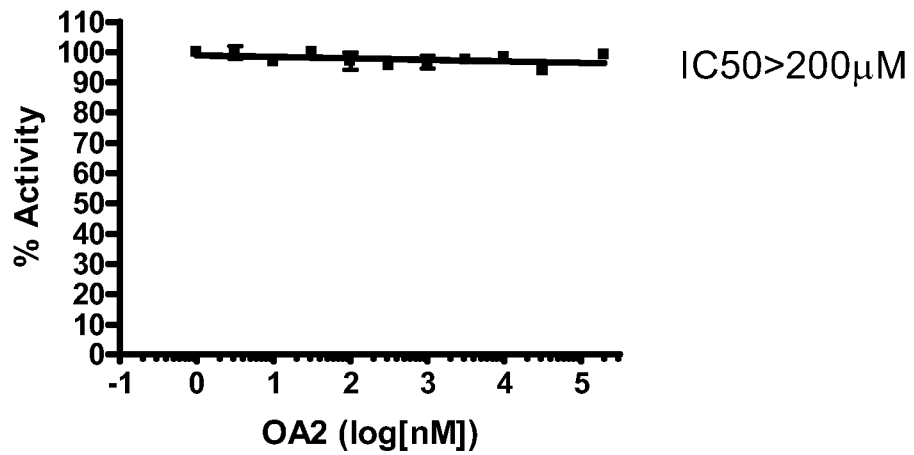
FIG. 11 is a graph showing the effect of OA2 (Compound 1) on Sirtuin2 activity.

FIG. 11 corresponds to the results shown in Table 12.

TABLE 13

HDAC6 Assay - Data for the Effect of Compound 1 on HDAC6 Activity

| Compound 1 (Log [nM]) | HDAC Activity (Fluorescence count) | | Background (Fluorescence count) | | % Activity | |
|---|---|---|---|---|---|---|
| | Repeat1 | Repeat2 | Repeat1 | Repeat2 | Repeat1 | Repeat2 |
| No CPD | 5844 | 5616 | 773 | 733 | 102.29 | 97.71 |
| 0.5 | 5998 | 6074 | 832 | 737 | 104.75 | 106.28 |
| 1.0 | 6006 | 5728 | 747 | 704 | 106.10 | 100.51 |
| 1.5 | 5541 | 6126 | 746 | 706 | 96.75 | 108.50 |
| 2.0 | 5733 | 5981 | 748 | 731 | 100.33 | 105.31 |
| 2.5 | 5678 | 5677 | 763 | 709 | 99.30 | 99.28 |
| 3.0 | 5717 | 5446 | 758 | 716 | 100.06 | 94.62 |
| 3.5 | 5575 | 5616 | 781 | 735 | 96.79 | 97.61 |
| 4.0 | 5516 | 5789 | 828 | 786 | 94.62 | 100.10 |
| 4.5 | 4994 | 5418 | 1081 | 1030 | 79.13 | 87.65 |
| 5.3 | 8327 | 9938 | 4925 | 4721 | 70.40 | 102.77 |

Figure 12:
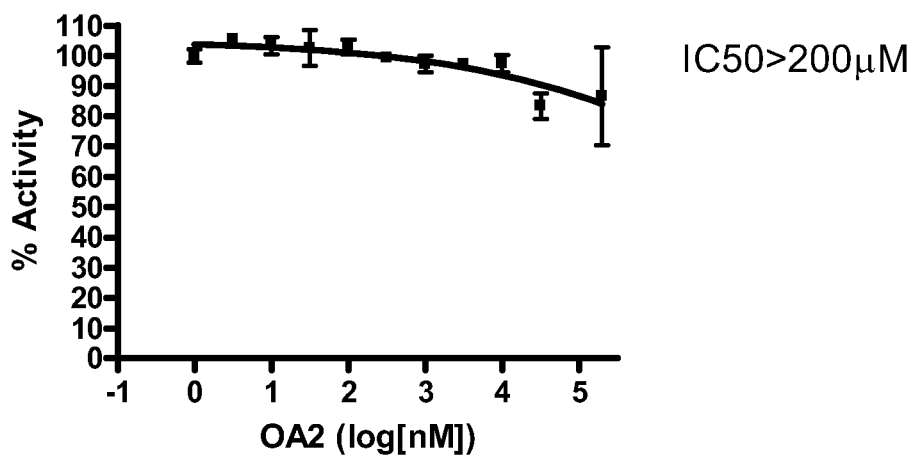
FIG. 12 is a graph showing the effect of OA2 (Compound 1) on HDAC6 activity.

FIG. 12 corresponds to the results shown in Table 13.

Results of Effect of SAHA on HDAC Inhibition

Figure 13:
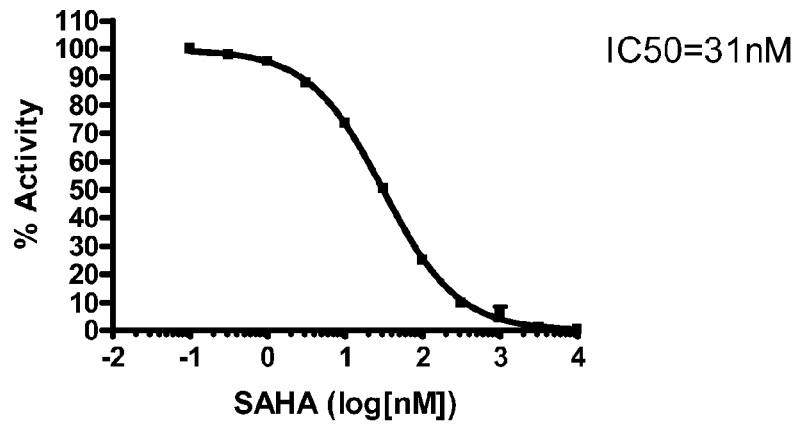
FIG. 13 is a graph showing the effect of the HDAC inhibitor, SAHA, on HDAC1 activity.
Figure 14:
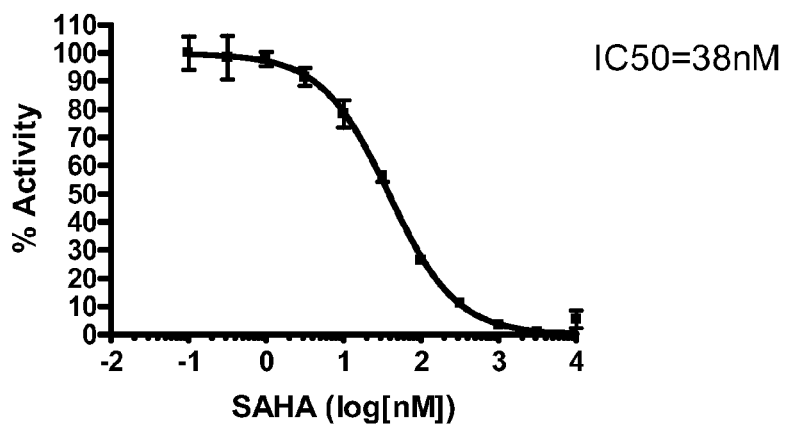
FIG. 14 is a graph showing the effect of the HDAC inhibitor, SAHA, on HDAC3/NCOR2 activity.
Figure 15:
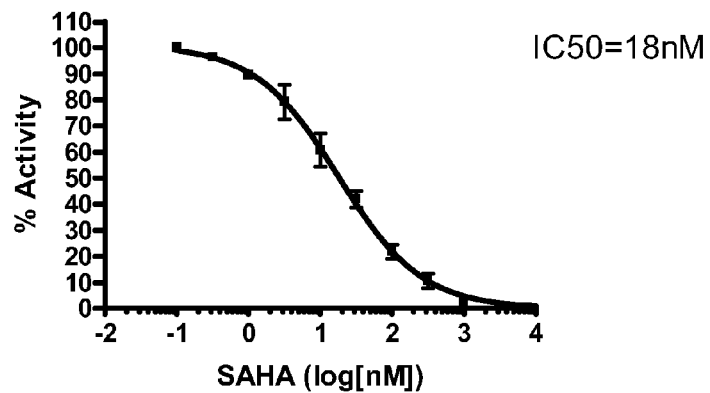
FIG. 15 is a graph showing the effect of the HDAC inhibitor, SAHA, on HDAC6 activity.

SAHA is an HDAC inhibitor (HDACi). It serves as a positive control for HDACs. FIGS. 13-15 show the inhibitory effect of SAHA on the HDACs HDAC1, HDAC3/NCOR2, and HDAC6. SAHA also inhibited HDAC5FL, HDAC7, HDAC8, HDAC10, Sirtuin 1, and Sirtuin 2 (see Table 1).

Figure 16:
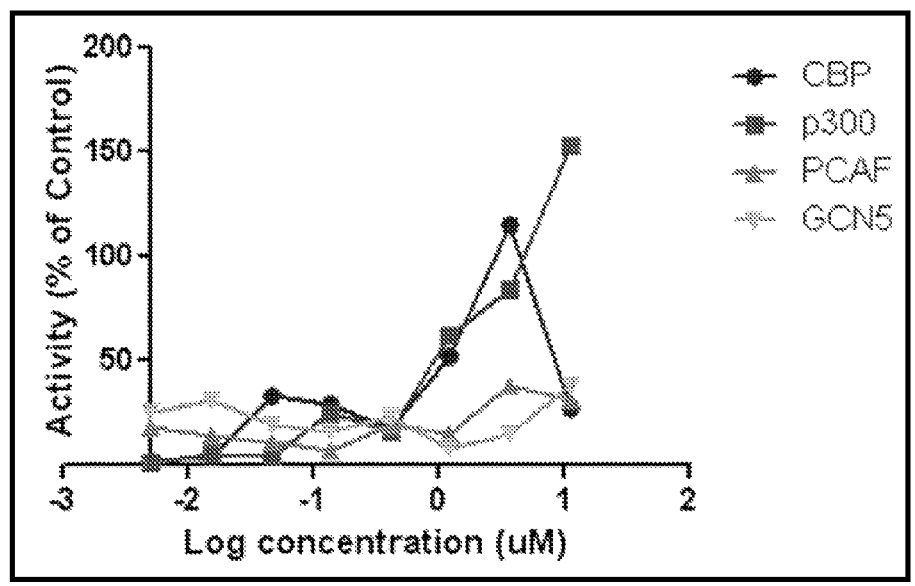
FIG. 16 shows dose-response curves for human CBP, p300, PCAF and GCN5 activation by different concentrations of Compound 1. Calculated Compound 1 $EC_{50}$ values for CBP, p300, PCAF and GCN5 are: 0.82 µM, 0.79 µM, 18.11 µM and 65.19 µM are respectively.

In In vitro assays, compound 1 has activity versus CBP, PCAF, and GCN5. The $EC_{50}$'s of compound 1 for CBP, PCAF, and GCN5 are 2.75 μM, 29.04 μM and 49.31 μM, respectively. Additionally, compound 1 did not interfere with p300 and HDAC activity (HDAC 1, 3, 5, 6, 7, 8, 10, 11, and sirt1-2). Compound 1 also increases p300 activity as shown in FIG. 16.

Example 4

Pharmacokinetic Experiments with Compound 1

Compound 1 pharmacokinetic (PK) and blood-brain barrier (BBB) penetration capability was assayed. After i.p. and i.v. administration at 20 mg/kg to BALB/c mice, plasma and brain concentrations were determined by LC-MS/MS. The data in Table 14 indicates that compound 1 is rapidly absorbed in the brain ($T_{max}$ at 15 min).

TABLE 14

Pharmacokinetic parameters of Compound 1.

| Parameters | IP Administration | | | IV Administration | | |
|---|---|---|---|---|---|---|
| | Plasma | Brain | Ratio* | Plasma | Brain | Ratio* |
| $T_{max}$ (h) | 0.25 | 0.25 | — | 0.125 | 0.125 | — |
| $C_{max}$ (ng/mL or ng/g) | 843 | 4878 | 5.8 | 2132 | 27892 | 13.1 |
| $AUC_{0-t}$ (ng · h/mL or ng · h/g) | 806 | 6493 | 8.1 | 1967 | 22222 | 11.3 |
| $AUC_{0-\infty}$ (ng · h/mL or ng · h/g) | 813 | 6564 | 8.1 | 2020 | 22581 | 11.2 |
| t½ (h) | 0.60 | 0.63 | — | 0.70 | 0.63 | — |
| MRT (h) | 0.85 | 1.03 | — | 0.84 | 0.74 | — |
| F (%) | 41.0 | 29.2 | — | — | — | — |

*Ratio = brain/plasma

YF2 $EC_{50}$'s for CBP, PCAF and GCN5 are: 2.75 μM, 29.04 μM and 49.31 μM, respectively The amount of compound 1 in the brain was higher than that in the plasma with an $AUC_{0-t}$ ratio of 8.2 and 10.8 for i.p. and i.v. administration, respectively. The elimination half-lives of compound 1 in the brain and plasma were ~40 min. The $T_{max}$ values in the brain and plasma were similar, indicating that the distribution of compound 1 to the brain is also fast. Additionally, in acute toxicity experiments compound 1 did not induce any adverse effects up to 300 mg/kg (i.p.).

Figure 17:
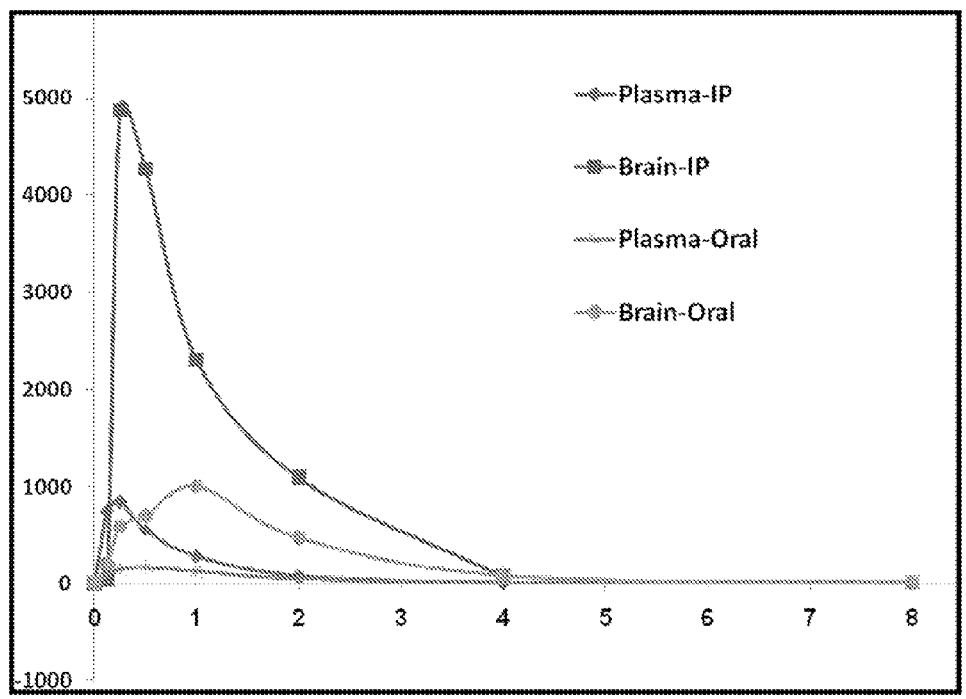
FIG. 17 is a graph showing pharmacokinetic properties of Compound 1. The amount of Compound 1 in the brain is higher than that in the plasma. Compound 1 is rapidly absorbed in the brain (see Table 14). The elimination half-lives of Compound 1 in the brain and plasma are ~40 min i.p. and 60 min. p.o. The distribution of Compound 1 to the brain is fast. Compound 1 does not induce any adverse effects up to 300 mg/kg (i.p.) in acute toxicity experiments. Chronic administration (45 days, i.p., daily, 20 mg/kg) of Compound 1 did not have adverse effects.

Pharmacokinetic properties of compound 1 dosed orally are shown in FIG. 17 and Table 15, and indicate that the amount of compound 1 in the brain is higher than that in the plasma.

TABLE 15

Oral pharmacokinetic parameters of Compound 1.

| Parameters | | Oral Administration | | |
|---|---|---|---|---|
| | | Plasma | Brain | Ratio* |
| $T_{max}$ | (h) | 0.5 | 1.0 | — |
| $C_{max}$ | (ng/mL or ng/g) | 177 | 1008 | 5.7 |
| $AUC_{0-t}$ | (ng · h/mL or ng · h/g) | 328 | 2149 | 6.6 |
| $AUC_{0-\infty}$ | (ng · h/mL or ng · h/g) | 330 | 2159 | 6.5 |
| t1/2 | (h) | 1.06 | 0.99 | — |
| MRT | (h) | 1.50 | 1.68 | — |

Example 5

Contextual Fear Conditioning Experiments

Contextual fear conditioning was performed to assess whether compound 1 is capable of enhancing memory. This type of cognitive test is much faster than other behavioral tasks that require multiple days of training and testing (*J Clin Invest*, 2004. 114(11): 1624-34; herein incorporated by reference in its entirety). The conditioning chamber was in a sound-attenuating box. A clear Plexiglas window allowed the experimenter to film the mouse performance with a camera placed on a tripod and connected to the Freezeframe software (MED Ass. Inc.). To provide background white noise (72 dB), a single computer fan was installed in one of the sides of the sound-attenuating chamber. The conditioning chamber had a 36-bar insulated shock grid floor. The floor was removable, and after each experimental subject, it was cleaned with 75% ethanol and then with water. Only one animal at a time was present in the experimentation MOM.

Training consisted of a 2.5 min period of acclimatizing to the context, followed by pairing of a tone (2800 Hz, 85 dB, 30 s) with a coterminating foot shock (0.4 mA, 1 s) for the weak training protocol, or pairing of a tone (2800 Hz, 85 dB, 30 s) with a coterminating foot shock (0.8 mA, 2 s) for the strong training protocol. The mice remained in the chamber for an additional 30 sec after the end of the last pairing, after which they were returned to their home cages. Contextual fear conditioning was assayed 24 hr after training by replacing the animals in the conditioning context for a 5 min period, during which the incidence of freezing (immobile except for respiration) was recorded.

The stronger training protocol leads to learning saturation, whereby freezing/memory reaches it max (~25-30% in WT animals) even if the foot shock is increased. On the other hand, the weaker training protocol leads to much less freezing (~15%), which allows the more freezing in case there is an increase in memory. When the weaker protocol was used, compound 1 worked as a memory enhancer.

Freezing behavior, defined as the absence of all movement except for that necessitated by breathing, was scored using the Freezeview software.

To evaluate contextual fear learning, freezing was measured for 5 min (consecutively) in the chamber in which the mice was trained 24 hr after training. To evaluate cued fear learning, following contextual testing, the mice were placed in a novel context (triangular cage with smooth flat floor) for 2 min (pre-CS test), after which they were exposed to the CS for 3 min (CS test), and freezing was measured. Sensory perception of the shock was determined through threshold assessment. A sequence of single foot shocks was delivered to animals placed on the same electrified grid used for fear conditioning. Initially, a 0.1 mV shock was delivered for 1 sec, and the animal behavior was evaluated for flinching, jumping, and vocalization. At 30 sec intervals the shock intensity was increased by 0.1 mV to 0.7 mV and then returned to 0 mV in 0.1 mV increments at 30 sec intervals. Threshold to vocalization, flinching, and then jumping was quantified for each animal by averaging the shock intensity at which each animal manifests a behavioral response to the foot shock.

Figure 18:
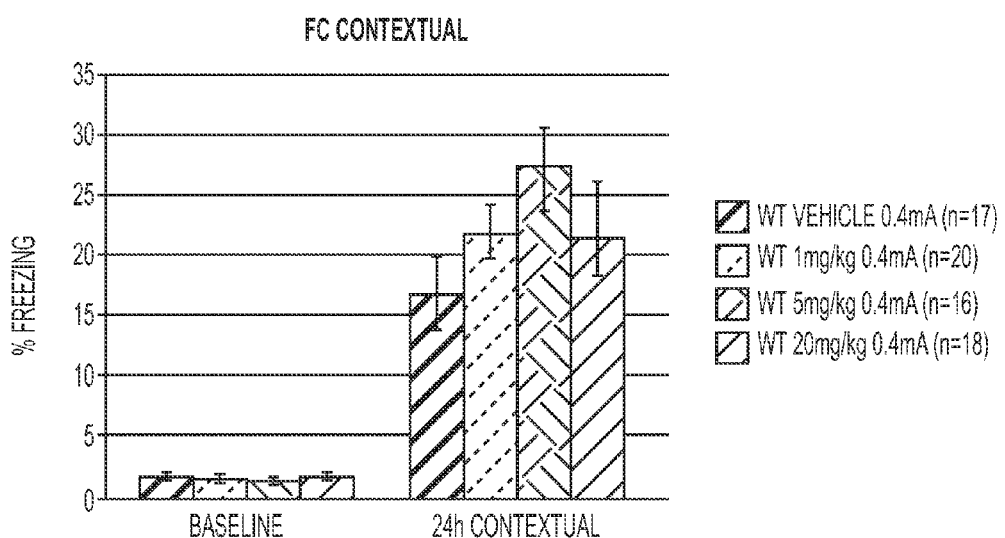
FIG. 18 is a bar graph demonstrating contextual fear conditioning responses after administration of Compound 1 (1, 5, and 20 mg/kg) to wild-type mice.
Figure 19:
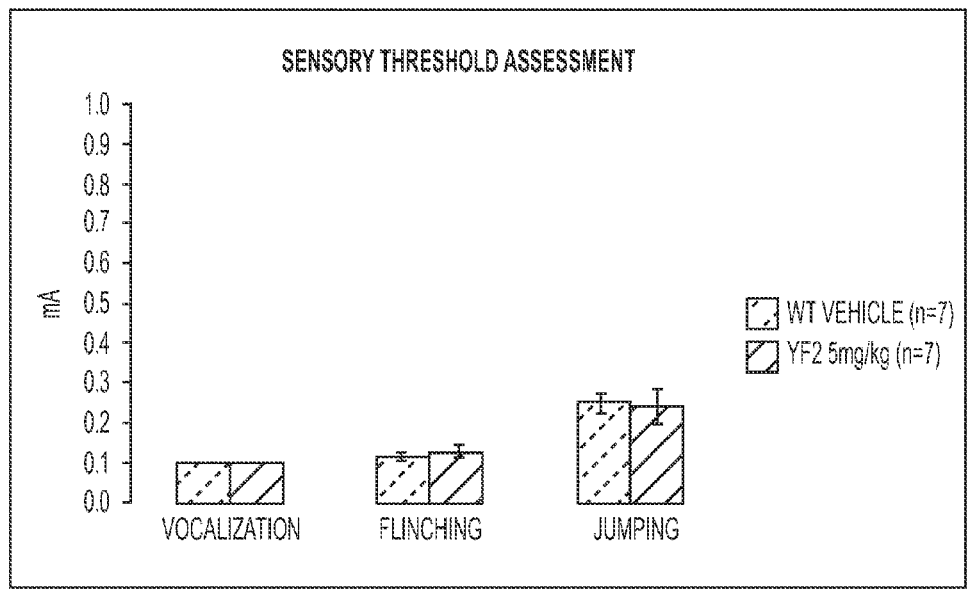
FIG. 19 is a bar graph demonstrating the assessment of sensory threshold in mice treated with vehicle or YF2 (Compound 1) (5 mg/kg).

Vehicle WT and compound 1 treated mice showed similar freezing responses before the delivery of the foot shock (baseline) (FIG. 18). However, 5 and 20 mg/kg compound 1 treated mice froze nearly twice as often as did WT vehicle mice 24 h after training protocol (a single pairing of a tone with a 0.35 mA foot shock). Finally, no difference was observed among different groups of mice in different sets of experiments in which we assessed sensory threshold in the presence of vehicle or compound 1 (YF2) alone (FIG. 19).

Figure 20:
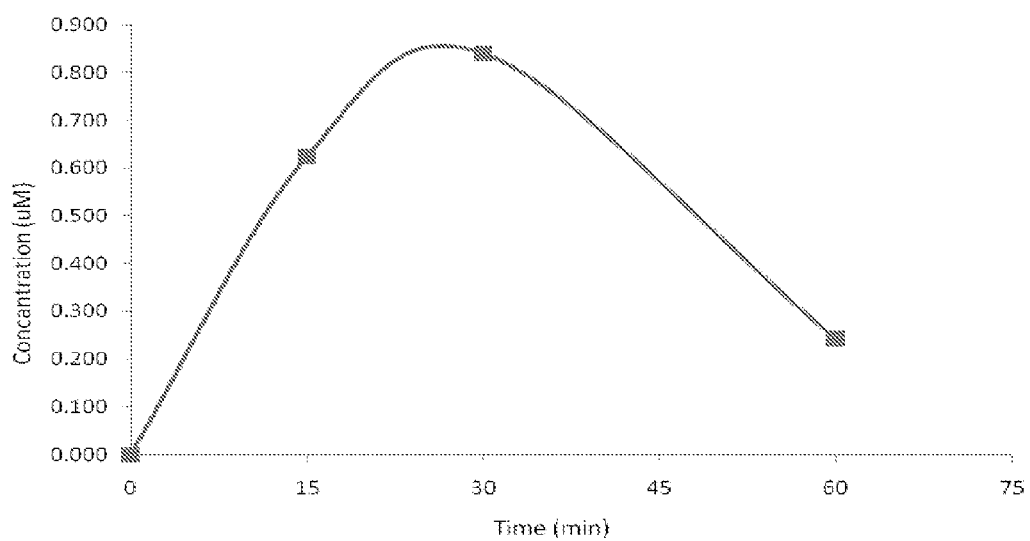
FIG. 20 is a graph showing the kinetics of the HAT agonist, Compound 1, in the blood. Compound 1 was administered (20 mg/kg. i.p.) to mice and then blood was sampled from tails at different time points.

Based on the results obtained during the fear conditioning tests, it was decided to determine the kinetics of compound 1 in blood to verify the best time point for treatment. To this purpose, compound 1 (20 mg/kg. i.p.) was administered and then sampled blood from tails at different time points. The kinetics of compound 1 shows a peak around 30 minutes post-injection (FIG. 20).

Figure 21:
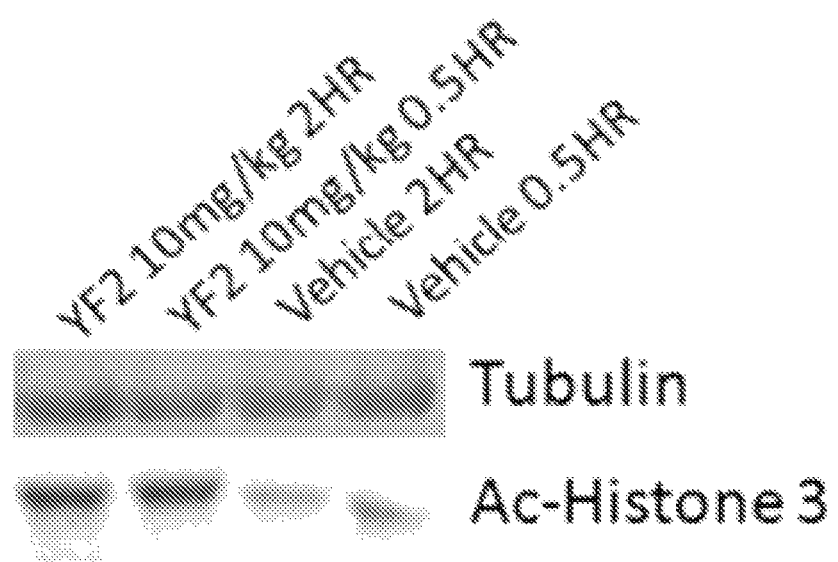
FIG. 21 is photograph of a western blot that shows histone 3 acetylation levels of mice hippocampus.

Compound 1, a Histone Acetyltransferase (HAT) Activator of the invention, is a good drug candidate to enhance memory and cognition in subjects without neurodegenerative diseases. When compound 1 (YF2) was administered to mice (i.p.), the western blot showed that it not only crosses the BBB, but also increases histone 3 acetylation levels of the hippocampus (FIG. 21).

Figure 22:
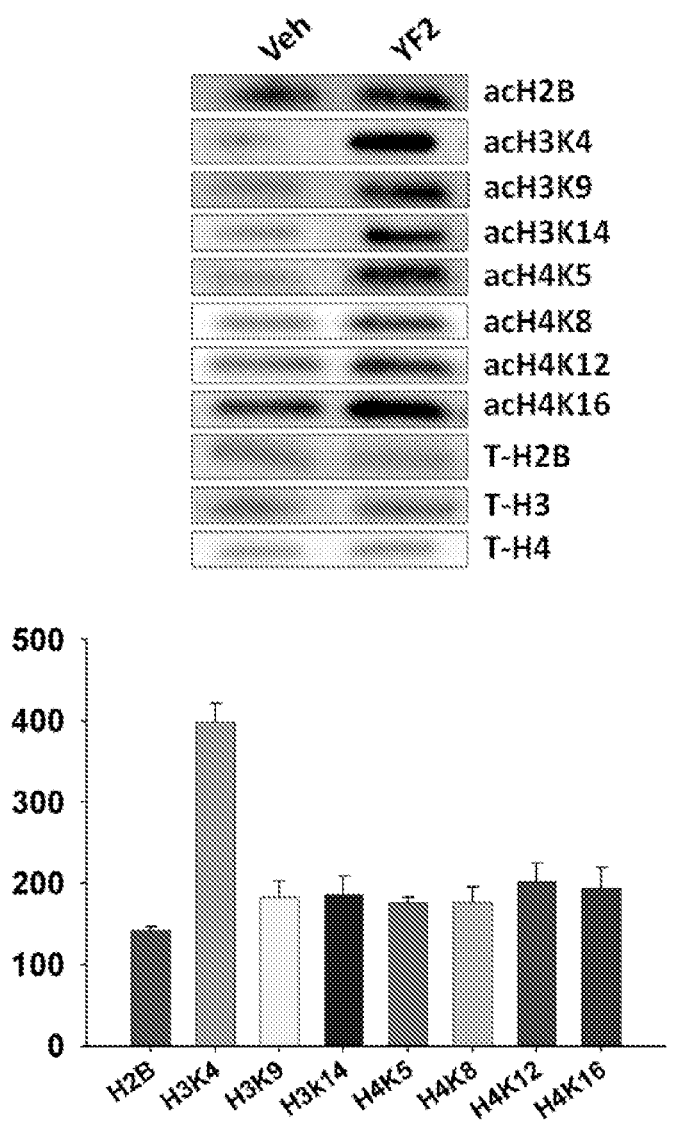
FIG. 22 shows that an acute administration of YF2 (Compound 1) increased specific acetylation of H3, H4, and H2B in hippocampal lysates. n=3 and p<0.05 per group.

Compound 1 was then tested to ascertain increases in histone acetylation in mouse hippocampus. The compound was i.p. administered at 20 mg/Kg, mice were sacrificed 30 min later, and hippocampi were removed and quickly frozen for WB analysis. As shown in FIG. 22, compound 1 (YF2) increased acetylation of histone lysines that were shown to be involved in memory formation (H3K4, H3K9, H3K14, H4K5, H4K8, H4K12, H4K16, and H2B) (*Neuron*, 2004, 42(6): 947-59; *Science* 328(5979): 753-6; each herein incorporated by reference in its entirety).

Example 6

Compound 1 Rescues Aβ-Induced Reduction in BDNF Levels

Compound 1 increases levels of BDNF, a key protein necessary for activity-dependent plasticity and memory. CBP was shown to facilitate the transcription of key proteins necessary for activity-dependent plasticity and memory (Korzus, E., M. G. Rosenfeld, and M. Mayford, *CBP histone acetyltransferase activity is a critical component of memory*

Figure 23:
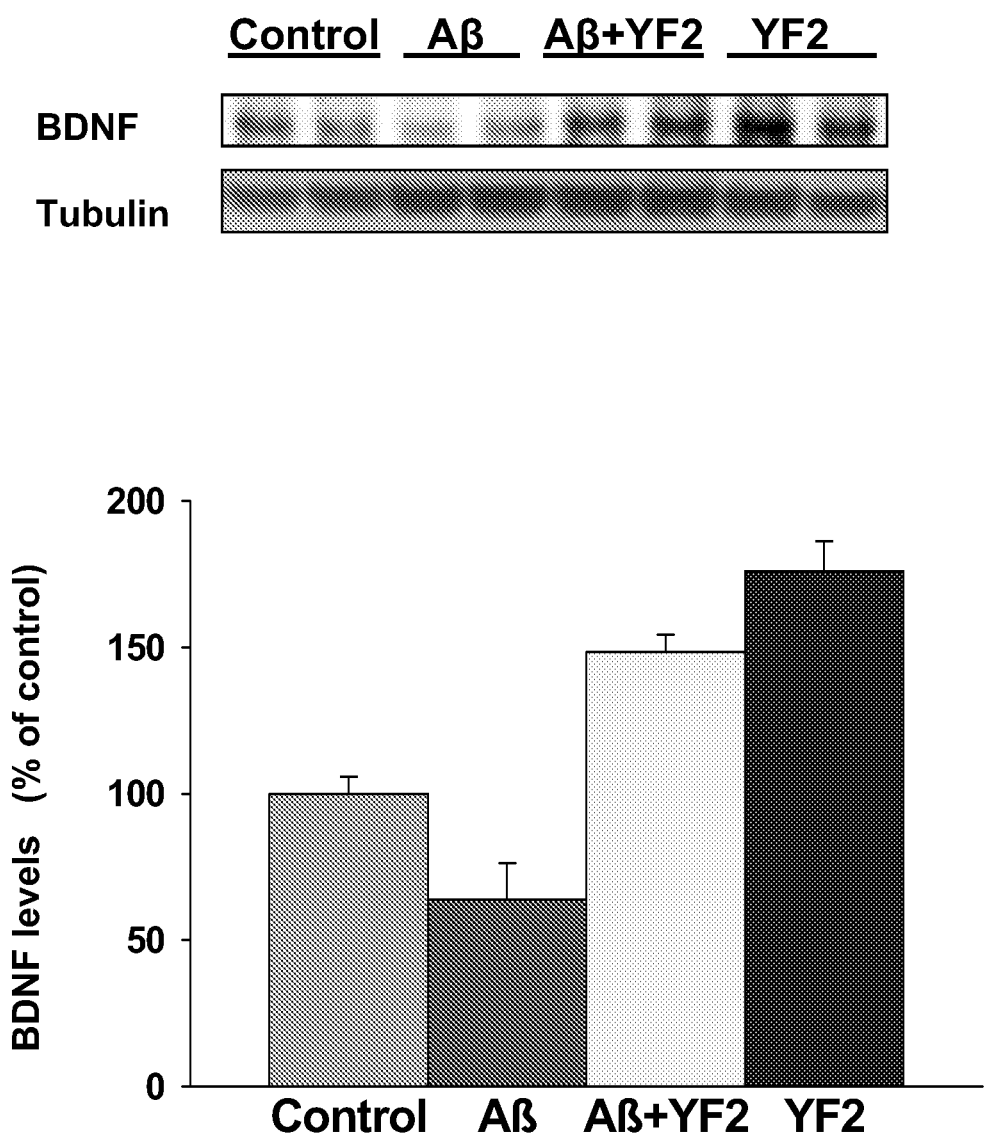
FIG. 23 shows beneficial effect of YF2 (Compound 1) on Ab42-induced reduction in BDNF levels. YF2 rescued Aβ-induced decrease in hippocampal BDNF levels (n=3 per each group, p<0.05). Aβ was infused through cannulas.

*consolidation*. Neuron, 2004. 42(6): p. 961-72; herein incorporated by reference in its entirety), such as brain-derived neurotrophic factor (BDNF), which is known to facilitate synaptic plasticity and memory formation (Cowansage, K. K., J. E. LeDoux, and M. H. Monfils, *Brain-derived neurotrophic factor: a dynamic gatekeeper of neural plasticity*. Current molecular pharmacology, 2010. 3(1): p. 12-29; Caccamo, A., et al., *CBP gene transfer increases BDNF levels and ameliorates learning and memory deficits in a mouse model of Alzheimer's disease*. Proc Natl Acad Sci USA, 2010. 107(52): p. 22687-92; each herein incorporated by reference in its entirety). Interestingly, BDNF was proposed to play a role in AD pathogenesis, with reduced BDNF levels detected in brains of AD patients and AD animal models (Hock, C., et al., *Region-specific neurotrophin imbalances in Alzheimer disease: decreased levels of brain-derived neurotrophic factor and increased levels of nerve growth factor in hippocampus and cortical areas*. Archives of neurology, 2000. 57(6): p. 846-51; Connor, B., et al., *Brain-derived neurotrophic factor is reduced in Alzheimer's disease*. Brain research. Molecular brain research, 1997. 49(1-2): p. 71-81; Garzon, D. J. and M. Fahnestock, *Oligomeric amyloid decreases basal levels of brain-derived neurotrophic factor (BDNF) mRNA via specific downregulation of BDNF transcripts IV and V in differentiated human neuroblastoma cells*. The Journal of Neuroscience: The Official Journal of the Society for Neuroscience, 2007. 27(10): p. 2628-35; each herein incorporated by reference in its entirety). Thus, preliminary studies on Compound 1 efficacy were extended to BDNF. BDNF levels in the hippocampi of Aβ-infused mice were measured compared to vehicle infused animals. Consistent with the decrease in BDNF levels in brains of AD patients and animal models of AD, a reduction of BDNF levels following Aβ infusion was found (FIG. 23). This effect was rescued by Compound 1 (20 mg/kg, i.p., 90 min before harvesting the hippocampi, FIG. 23). Interestingly, Compound 1 increased BDNF levels in vehicle-infused mice (FIG. 23), consistent with the observation that basal levels of BDNF are increased following stimulation of the gene transcription machinery relevant to memory formation (Arancio, O. and M. V. Chao, *Neurotrophins, synaptic plasticity and dementia*. Current Opinion in Neurobiology, 2007. 17(3): p. 325-30; herein incorporated by reference in its entirety).

Those skilled in the art will recognize, or be able to ascertain, using no more than routine experimentation, numerous equivalents to the specific substances and procedures described herein. Such equivalents are considered to be within the scope of this invention, and are covered by the following claims.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways to obtain additional embodiments within the scope and spirit of the invention.

What is claimed:

1. A method for treating memory loss or a learning disability in a subject in need thereof, which comprises administering to the subject a therapeutically effective amount of compound (I):

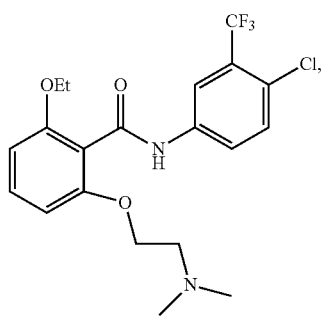

(I)

or a pharmaceutically acceptable salt thereof, wherein the subject is not afflicted with a neurodegenerative condition or disease.

2. The method of claim 1, wherein the neurodegenerative condition or disease is selected from the group consisting of adrenoleukodystrophy (ALD), alcoholism, Alexander's disease, Alper's disease, Alzheimer's disease, amyotrophic lateral sclerosis (Lou Gehrig's Disease or ALS), ataxia telangiectasia, batten disease (Spielmeyer-Vogt-Sjogren-Batten disease), bovine spongiform encephalopathy (BSE), canavan disease, cockayne syndrome, corticobasal degeneration, Creutzfeldt-Jakob disease, familial fatal insomnia, frontotemporal lobar degeneration, Huntington's disease, HIV-associated dementia, Kennedy's disease, Krabbe's disease, lewy body dementia, neuroborreliosis, Machado-Joseph disease (spinocerebellar ataxia type 3), multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Rett's syndrome, tau-positive frontotemporal dementia, tau-negative frontotemporal dementia, Refsum's disease, sandhoff disease, Schilder's disease, subacute combined degeneration of spinal cord secondary to pernicious anaemia, spinocerebellar ataxia, spinal muscular atrophy, Steele-Richardson-Olszewski disease, Tabes dorsalis, and toxic encephalopathy.

3. The method of claim 1, wherein the neurodegenerative condition or disease is Alzheimer's.

4. The method of claim 1, wherein the subject is a mammal.

5. The method of claim 1, wherein the therapeutically effective amount is at least about 1 mg/kg body weight.

6. The method of claim 1, wherein the therapeutically effective amount is at least 1 mg/kg body weight.

* * * * *

UNITED STATES PATENT AND TRADEMARK OFFICE
CERTIFICATE OF CORRECTION

PATENT NO.         : 9,809,532 B2
APPLICATION NO.    : 14/125214
DATED              : November 7, 2017
INVENTOR(S)        : Yitshak Francis et al.

It is certified that error appears in the above-identified patent and that said Letters Patent is hereby corrected as shown below:

In the Specification

Column 1 Lines 14-18 should read:
This invention was made with government support under NS049442 and AG034248 awarded by the National Institutes of Health. The government has certain rights in the invention.

Signed and Sealed this
Twenty-eighth Day of January, 2020

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 419
<212> TYPE: PRT
<213> ORGANISM: Homo sapiens

<400> SEQUENCE: 1

Met Ala Gly Phe Gly Ala Met Glu Lys Phe Leu Val Glu Tyr Lys Ser
1               5                   10                  15

Ala Val Glu Lys Lys Leu Ala Glu Tyr Lys Cys Asn Thr Asn Thr Ala
            20                  25                  30

Ile Glu Leu Lys Leu Val Arg Phe Pro Glu Asp Leu Glu Asn Asp Ile
        35                  40                  45

Arg Thr Phe Phe Pro Glu Tyr Thr His Gln Leu Phe Gly Asp Asp Glu
    50                  55                  60

Thr Ala Phe Gly Tyr Lys Gly Leu Lys Ile Leu Leu Tyr Tyr Ile Ala
65                  70                  75                  80

Gly Ser Leu Ser Thr Met Phe Arg Val Glu Tyr Ala Ser Lys Val Asp
                85                  90                  95

Glu Asn Phe Asp Cys Val Glu Ala Asp Asp Val Glu Gly Lys Ile Arg
            100                 105                 110

Gln Ile Ile Pro Pro Gly Phe Cys Thr Asn Thr Asn Asp Phe Leu Ser
        115                 120                 125

Leu Leu Glu Lys Glu Val Asp Phe Lys Pro Phe Gly Thr Leu Leu His
    130                 135                 140

Thr Tyr Ser Val Leu Ser Pro Thr Gly Gly Glu Asn Phe Thr Phe Gln
145                 150                 155                 160

Ile Tyr Lys Ala Asp Met Thr Cys Arg Gly Phe Arg Glu Tyr His Glu
```

```
                       165                 170                 175
Arg Leu Gln Thr Phe Leu Met Trp Phe Ile Glu Thr Ala Ser Phe Ile
                180                 185                 190

Asp Val Asp Asp Glu Arg Trp His Tyr Phe Leu Val Phe Glu Lys Tyr
            195                 200                 205

Asn Lys Asp Gly Ala Thr Leu Phe Ala Thr Val Gly Tyr Met Thr Val
        210                 215                 220

Tyr Asn Tyr Tyr Val Tyr Pro Asp Lys Thr Arg Pro Arg Val Ser Gln
225                 230                 235                 240

Met Leu Ile Leu Thr Pro Phe Gln Gly Gln Gly His Gly Ala Gln Leu
                245                 250                 255

Leu Glu Thr Val His Arg Tyr Tyr Thr Glu Phe Pro Thr Val Leu Asp
            260                 265                 270

Ile Thr Ala Glu Asp Pro Ser Lys Ser Tyr Val Lys Leu Arg Asp Phe
        275                 280                 285

Val Leu Val Lys Leu Cys Gln Asp Leu Pro Cys Phe Ser Arg Glu Lys
        290                 295                 300

Leu Met Gln Gly Phe Asn Glu Asp Met Ala Ile Glu Ala Gln Gln Lys
305                 310                 315                 320

Phe Lys Ile Asn Lys Gln His Ala Arg Arg Val Tyr Glu Ile Leu Arg
                325                 330                 335

Leu Leu Val Thr Asp Met Ser Asp Ala Glu Gln Tyr Arg Ser Tyr Arg
            340                 345                 350

Leu Asp Ile Lys Arg Arg Leu Ile Ser Pro Tyr Lys Lys Gln Arg
        355                 360                 365

Asp Leu Ala Lys Met Arg Lys Cys Leu Arg Pro Glu Glu Leu Thr Asn
        370                 375                 380

Gln Met Asn Gln Ile Glu Ile Ser Met Gln His Glu Gln Leu Glu Glu
385                 390                 395                 400

Ser Phe Gln Glu Leu Val Glu Asp Tyr Arg Arg Val Ile Glu Arg Leu
                405                 410                 415

Ala Gln Glu

<210> SEQ ID NO 2
<211> LENGTH: 1682
<212> TYPE: DNA
<213> ORGANISM: Homo sapiens

<400> SEQUENCE: 2
ctgtgcggtc acttccggcc cgggagcgcg cgggttgatt cgtccttcct cagccgcggg      60
tgatcgtagc tcggaaatgg cgggatttgg tgctatggag aaattttttgg tagaatataa     120 gagtgcagtg gagaagaaac tggcagagta caaatgtaac accaacacag caattgaact    180
aaaattagtt cgttttcctg aagatcttga aaatgacatt agaactttct ttcctgagta    240
tacccatcaa ctctttgggg atgatgaaac tgcttttggt tacaagggtc taaagatcct    300
gttatactat attgctggta gcctgtcaac aatgttccgt gttgaatatg catctaaagt    360
tgatgagaac tttgactgtg tagaggcaga tgatgttgag ggcaaaatta gacaaatcat    420
tccacctgga ttttgcacaa acacgaatga tttcctttct ttactggaaa aggaagttga    480
tttcaagcca ttcggaacct tacttcatac ctactcagtt ctcagtccaa caggaggaga    540
aaactttacc tttcagatat ataaggctga catgacatgt agaggctttc gagaatatca    600
tgaaaggctt cagacctttt tgatgtggtt tattgaaact gctagcttta ttgacgtgga    660
```

```
tgatgaaaga tggcactact ttctagtatt tgagaagtat aataaggatg gagctacgct   720
ctttgcgacc gtaggctaca tgacagtcta taattactat gtgtacccag acaaaacccg   780
gccacgtgta agtcagatgc tgattttgac tccatttcaa ggtcaaggcc atggtgctca   840
acttcttgaa acagttcata gatactcac tgaatttcct acagttcttg atattacagc    900
```

```
tgatgaaaga tggcactact ttctagtatt tgagaagtat aataaggatg gagctacgct   720
ctttgcgacc gtaggctaca tgacagtcta taattactat gtgtacccag acaaaacccg   780
gccacgtgta agtcagatgc tgattttgac tccatttcaa ggtcaaggcc atggtgctca   840
acttcttgaa acagttcata gatactcac tgaatttcct acagttcttg atattacagc    900
ggaagatcca tccaaaagct atgtgaaatt acgagacttt gtgcttgtga agctttgtca    960
agatttgccc tgttttccc gggaaaaatt aatgcaagga ttcaatgaag atatggcgat   1020
agaggcacaa cagaagttca aaataaataa gcaacacgct agaagggttt atgaaattct   1080
tcgactactg gtaactgaca tgagtgatgc cgaacaatac agaagctaca gactggatat   1140
taaaagaaga ctaattagcc catataagaa aaagcagaga gatcttgcta agatgagaaa   1200
atgtctcaga ccagaagaac tgacaaacca gatgaaccaa atagaaataa gcatgcaaca   1260
tgaacagctg gaagagagtt ttcaggaact agtggaagat taccggcgtg ttattgaacg   1320
acttgctcaa gagtaaagat tatactgctc tgtacaggaa gcttgcaaat tttctgtaca   1380
atgtgctgtg aaaaatctga tgactttaat tttaaaatct tgtgacattt tgcttatact   1440
aaaagttatc tatctttagt tgaatatttt cttttggaga gattgtatat tttaaaatac   1500
tgtttagagt ttatgagcat atattgcatt taaagaaaga taaagcttct gaaatactac   1560
tgcaattgct tcccttctta aacagtataa taaatgctta gttgtgatat gttaatgtgt   1620
gatgatatga ttcttaaata cttacaataa acctcattct taaatactta aaaaaaaaaa   1680
aa                                                                  1682
```

<210> SEQ ID NO 3
<211> LENGTH: 832
<212> TYPE: PRT
<213> ORGANISM: Homo sapiens

<400> SEQUENCE: 3

Met Ser Glu Ala Gly Gly Ala Gly Pro Gly Gly Cys Gly Ala Gly Ala
1               5                   10                  15

Gly Ala Gly Ala Gly Pro Gly Ala Leu Pro Pro Gln Pro Ala Ala Leu
            20                  25                  30

Pro Pro Ala Pro Pro Gln Gly Ser Pro Cys Ala Ala Ala Ala Gly Gly
        35                  40                  45

Ser Gly Ala Cys Gly Pro Ala Thr Ala Val Ala Ala Gly Thr Ala
    50                  55                  60

Glu Gly Pro Gly Gly Gly Gly Ser Ala Arg Ile Ala Val Lys Lys Ala
65                  70                  75                  80

Gln Leu Arg Ser Ala Pro Arg Ala Lys Lys Leu Glu Lys Leu Gly Val
                85                  90                  95

Tyr Ser Ala Cys Lys Ala Glu Glu Ser Cys Lys Cys Asn Gly Trp Lys
            100                 105                 110

Asn Pro Asn Pro Ser Pro Thr Pro Pro Arg Ala Asp Leu Gln Gln Ile
        115                 120                 125

Ile Val Ser Leu Thr Glu Ser Cys Arg Ser Cys Ser His Ala Leu Ala
    130                 135                 140

Ala His Val Ser His Leu Glu Asn Val Ser Glu Glu Met Asn Arg
145                 150                 155                 160

Leu Leu Gly Ile Val Leu Asp Val Glu Tyr Leu Phe Thr Cys Val His
                165                 170                 175

Lys Glu Glu Asp Ala Asp Thr Lys Gln Val Tyr Phe Tyr Leu Phe Lys
            180                 185                 190

```
Leu Leu Arg Lys Ser Ile Leu Gln Arg Gly Lys Pro Val Glu Gly
            195                 200                 205

Ser Leu Glu Lys Lys Pro Pro Phe Glu Lys Pro Ser Ile Glu Gln Gly
    210                 215                 220

Val Asn Asn Phe Val Gln Tyr Lys Phe Ser His Leu Pro Ala Lys Glu
225                 230                 235                 240

Arg Gln Thr Ile Val Glu Leu Ala Lys Met Phe Leu Asn Arg Ile Asn
                245                 250                 255

Tyr Trp His Leu Glu Ala Pro Ser Gln Arg Arg Leu Arg Ser Pro Asn
                260                 265                 270

Asp Asp Ile Ser Gly Tyr Lys Glu Asn Tyr Thr Arg Trp Leu Cys Tyr
                275                 280                 285

Cys Asn Val Pro Gln Phe Cys Asp Ser Leu Pro Arg Tyr Glu Thr Thr
                290                 295                 300

Gln Val Phe Gly Arg Thr Leu Leu Arg Ser Val Phe Thr Val Met Arg
305                 310                 315                 320

Arg Gln Leu Leu Glu Gln Ala Arg Gln Glu Lys Asp Lys Leu Pro Leu
                325                 330                 335

Glu Lys Arg Thr Leu Ile Leu Thr His Phe Pro Lys Phe Leu Ser Met
                340                 345                 350

Leu Glu Glu Glu Val Tyr Ser Gln Asn Ser Pro Ile Trp Asp Gln Asp
                355                 360                 365

Phe Leu Ser Ala Ser Ser Arg Thr Ser Gln Leu Gly Ile Gln Thr Val
                370                 375                 380

Ile Asn Pro Pro Val Ala Gly Thr Ile Ser Tyr Asn Ser Thr Ser
385                 390                 395                 400

Ser Ser Leu Glu Gln Pro Asn Ala Gly Ser Ser Ser Pro Ala Cys Lys
                405                 410                 415

Ala Ser Ser Gly Leu Glu Ala Asn Pro Gly Glu Lys Arg Lys Met Thr
                420                 425                 430

Asp Ser His Val Leu Glu Glu Ala Lys Lys Pro Arg Val Met Gly Asp
                435                 440                 445

Ile Pro Met Glu Leu Ile Asn Glu Val Met Ser Thr Ile Thr Asp Pro
                450                 455                 460

Ala Ala Met Leu Gly Pro Glu Thr Asn Phe Leu Ser Ala His Ser Ala
465                 470                 475                 480

Arg Asp Glu Ala Ala Arg Leu Glu Glu Arg Arg Gly Val Ile Glu Phe
                485                 490                 495

His Val Val Gly Asn Ser Leu Asn Gln Lys Pro Asn Lys Lys Ile Leu
                500                 505                 510

Met Trp Leu Val Gly Leu Gln Asn Val Phe Ser His Gln Leu Pro Arg
                515                 520                 525

Met Pro Lys Glu Tyr Ile Thr Arg Leu Val Phe Asp Pro Lys His Lys
    530                 535                 540

Thr Leu Ala Leu Ile Lys Asp Gly Arg Val Ile Gly Gly Ile Cys Phe
545                 550                 555                 560

Arg Met Phe Pro Ser Gln Gly Phe Thr Glu Ile Val Phe Cys Ala Val
                565                 570                 575

Thr Ser Asn Glu Gln Val Lys Gly Tyr Gly Thr His Leu Met Asn His
                580                 585                 590

Leu Lys Glu Tyr His Ile Lys His Asp Ile Leu Asn Phe Leu Thr Tyr
                595                 600                 605
```

```
Ala Asp Glu Tyr Ala Ile Gly Tyr Phe Lys Lys Gln Gly Phe Ser Lys
    610                 615                 620
Glu Ile Lys Ile Pro Lys Thr Lys Tyr Val Gly Tyr Ile Lys Asp Tyr
625                 630                 635                 640
Glu Gly Ala Thr Leu Met Gly Cys Glu Leu Asn Pro Arg Ile Pro Tyr
                645                 650                 655
Thr Glu Phe Ser Val Ile Ile Lys Lys Gln Lys Glu Ile Ile Lys Lys
            660                 665                 670
Leu Ile Glu Arg Lys Gln Ala Gln Ile Arg Lys Val Tyr Pro Gly Leu
        675                 680                 685
Ser Cys Phe Lys Asp Gly Val Arg Gln Ile Pro Ile Glu Ser Ile Pro
    690                 695                 700
Gly Ile Arg Glu Thr Gly Trp Lys Pro Ser Gly Lys Glu Lys Ser Lys
705                 710                 715                 720
Glu Pro Arg Asp Pro Asp Gln Leu Tyr Ser Thr Leu Lys Ser Ile Leu
                725                 730                 735
Gln Gln Val Lys Ser His Gln Ser Ala Trp Pro Phe Met Glu Pro Val
            740                 745                 750
Lys Arg Thr Glu Ala Pro Gly Tyr Tyr Glu Val Ile Arg Phe Pro Met
        755                 760                 765
Asp Leu Lys Thr Met Ser Glu Arg Leu Lys Asn Arg Tyr Tyr Val Ser
    770                 775                 780
Lys Lys Leu Phe Met Ala Asp Leu Gln Arg Val Phe Thr Asn Cys Lys
785                 790                 795                 800
Glu Tyr Asn Pro Pro Glu Ser Glu Tyr Tyr Lys Cys Ala Asn Ile Leu
                805                 810                 815
Glu Lys Phe Phe Phe Ser Lys Ile Lys Glu Ala Gly Leu Ile Asp Lys
            820                 825                 830

<210> SEQ ID NO 4
<211> LENGTH: 4824
<212> TYPE: DNA
<213> ORGANISM: Homo sapiens

<400> SEQUENCE: 4
gcggaaaaga ggccgtgggg ggcctcccag cgctggcaga caccgtgagg ctggcagccg    60
ccggcacgca cacctagtcc gcagtcccga ggaacatgtc cgcagccagg gcgcggagca   120
gagtcccggg caggagaacc aagggagggc gtgtgctgtg gcggcggcgg cagcggcagc   180
ggagccgcta gtccctccc tcctggggga gcagctgccg ccgctgccgc cgccgccacc   240
accatcagcg cgcggggccc ggccagagcg agccgggcga gcggcgcgct agggggaggg   300
cggggggcggg gaggggggtg ggcgaagggg gcggagggc gtgggggag ggtctcgctc   360
tcccgactac cagagcccga gagggagacc ctggcggcgg cggcggcgcc tgacactcgg   420
cgcctcctgc cgtgctccgg ggcggcatgt ccgaggctgg cggggccggg ccgggcggct   480
gcggggcagg agccggggca ggggccgggc ccgggcgct gccccgcag cctgcggcgc   540
ttccgcccgc gccccgcag ggctccccct gcgccgctgc cgccggggc tcgggcgcct   600
gcggtccggc gacggcagtg gctgcagcgg gcacggccga aggaccggga ggcggtggct   660
cggcccgaat cgccgtgaag aaagcgcaac tacgctccgc tccgcgggcc aagaaactgg   720
agaaactcgg agtgtactcc gcctgcaagg ccgaggagtc ttgtaaatgt aatggctgga   780
aaacccctaa cccctcaccc actccccca gagccgacct gcagcaaata attgtcagtc   840
taacagaatc ctgtcggagt tgtagccatg ccctagctgc tcatgtttcc cacctggaga   900
```

```
atgtgtcaga ggaagaaatg aacagactcc tgggaatagt attggatgtg aatatctct     960
ttacctgtgt ccacaaggaa gaagatgcag ataccaaaca agtttatttc tatctattta    1020
agctcttgag aaagtctatt ttacaaagag gaaaacctgt ggttgaaggc tctttggaaa    1080
agaaaccccc atttgaaaaa cctagcattg aacagggtgt gaataacttt gtgcagtaca    1140
aatttagtca cctgccagca aaagaaaggc aaacaatagt tgagttggca aaaatgttcc    1200
taaaccgcat caactattgg catctggagg caccatctca acgaagactg cgatctccca    1260
atgatgatat ttctggatac aaagagaact acacaaggtg gctgtgttac tgcaacgtgc    1320
cacagttctg cgacagtcta cctcggtacg aaaccacaca ggtgtttggg agaacattgc    1380
ttcgctcggt cttcactgtt atgaggcgac aactcctgga caagcaaga caggaaaaag    1440
ataaactgcc tcttgaaaaa cgaactctaa tcctcactca tttcccaaaa tttctgtcca    1500
tgctagaaga agaagtatat agtcaaaact ctcccatctg ggatcaggat tttctctcag    1560
cctcttccag aaccagccag ctaggcatcc aaacagttat caatccacct cctgtggctg    1620
ggacaatttc atacaattca acctcatctt cccttgagca gccaaacgca gggagcagca    1680
gtcctgcctg caaagcctct tctggacttg aggcaaaccc aggagaaaag aggaaaatga    1740
ctgattctca tgttctggag gaggccaaga accccgagt tatgggggat attccgatgg    1800
aattaatcaa cgaggttatg tctaccatca cggaccctgc agcaatgctt ggaccagaga    1860
ccaattttct gtcagcacac tcggccaggg atgaggcggc aaggttggaa gagcgcaggg    1920
gtgtaattga atttcacgtg gttggcaatt ccctcaacca gaaaccaaac aagaagatcc    1980
tgatgtggct ggttggccta cagaacgttt tctcccacca gctgccccga atgccaaaag    2040
aatacatcac acggctcgtc tttgacccga acacaaaac ccttgcttta attaaagatg    2100
gccgtgttat tggtggtatc tgtttccgta tgttcccatc tcaaggattc acagagattg    2160
tcttctgtgc tgtaacctca aatgagcaag tcaagggcta tggaacacac ctgatgaatc    2220
atttgaaaga atatcacata aagcatgaca tcctgaactt cctcacatat gcagatgaat    2280
atgcaattgg atactttaag aaacagggtt tctccaaaga aattaaaata cctaaaacca    2340
aatatgttgg ctatatcaag gattatgaag gagccacttt aatgggatgt gagctaaatc    2400
cacggatccc gtacacagaa ttttctgtca tcattaaaaa gcagaaggag ataattaaaa    2460
aactgattga aagaaaacag gcacaaattc gaaaagttta ccctggactt tcatgtttta    2520
aagatggagt tcgacagatt cctatagaaa gcattcctgg aattagagag acaggctgga    2580
aaccgagtgg aaaagagaaa agtaaagagc ccagagaccc tgaccagctt tacagcacgc    2640
tcaagagcat cctccagcag gtgaagagcc atcaaagcgc ttggcccttc atggaacctg    2700
tgaagagaac agaagctcca ggatattatg aagttataag gttccccatg gatctgaaaa    2760
ccatgagtga acgcctcaag aataggtact acgtgtctaa gaaattattc atggcagact    2820
tacagcgagt ctttaccaat tgcaaagagt acaaccccc tgagagtgaa tactacaaat    2880
gtgccaatat cctggagaaa ttcttcttca gtaaaattaa ggaagctgga ttaattgaca    2940
agtgattttt tttcccctct gcttcttaga aactccaccaa gcagtgtgcc taaagcaagg    3000
tggtttagtt ttttacaaag aattggacat gatgtattga agagacttgt aaatgtaata    3060
attagcactt tgaaaaaac aaaaaaccte cttttagctt ttcagatatg tatttaaatt    3120
gaagtcatag gacatttta ttttatggaa tagattttaa tctatttact actattaagg    3180
taaattttct atggcatgtc cattagctat ttcatgatag atgattaggg gtttcctcaa    3240
```

-continued

```
aacctgtgtg tgaggaaatt gcacacagta gcaaaatttg gggaaatcca taacattttc    3300
agaccatgaa tgaatgtttc cattttttc taatggaatg tgagagttta cttttatttt     3360
attctgaagg actttaagga agggatacat gattttaaaa aagcctgtaa gaggtgaaat    3420
atgtgatgtt tgaagtctct ttatagactt tttatatata tttttttaaaa cactcatcta   3480 gatgaggtgc tttgagcagt tctgaaaaat gcagttccag gaaagcaact gctttggttc    3540
ctaaggaaga aattctaaat aatgcaaact tttaaaataa gcatctaggt ttttgataat    3600
tctgtctact tacaacaaac ttgttagtac ataaccacta tttaataat tattttctct     3660 acacaaatgt gtaatatcat atttgacttt gcttatgcag gccataagtt ccaaaagata    3720
atttccctgc ccacaaaggc ataaacttga aaacacatga gattgaatca acatgcttta    3780
ataggaaaag atgtatggtc tatatatgta tcaatctggt gaatcctcgt tctaataaag    3840 gttcttttc tttctatga tacacacagc cacgctgata atatgcaaat gaacattttc      3900
ctttatgtct ctccagataa tgtttattgt ctgaggtaaa ttaaattccc accagggttt    3960
gctgtcagta ttttaacacc cacattagta tatgcgtcca gggtcataac cccctaaaat    4020
ccatcatgca accttattaa tctgtcttgg gattccagtt tagtgcttgg attattttcc    4080
tgattacact acatagaaaa gtgagacatc tgccattccc aactctggga aaaccaacta    4140
atatacaacc atataaatga aggccatctt gatggtctca acactaattt ttatgatgca    4200
aatttataca ctgattttg taaaggacaa agttttaaaa gcgtatttaa cttgatgttt     4260
tctatcagca taaataaaat ggtcatgaat agtcattaaa aacagttgcc agtgataatc    4320
tgcatgaagg aaaaagaacc ctgcaaatgg ctattgagtt ggaagtattg tttttgatat    4380
gtaagagata ttcagaatgc tcacactgaa aatgcctcaa cttttaaag tgtaagaaac     4440 caccatgagt ggtgtctaga tttctaatga agaatcatga tacagtttgg attaagtatc    4500
ttggactggt tttaaacagt gctttgtacc ggatctgctg aagcatctgt ccagctggta    4560
tcctgtgaaa gtttgttatt ttctgagtag acattcttat agagtattgt ctttaaaatc    4620
agattgtctc ttctatattg aaagcatttt tatgttttct aatttaaaaa ttaatatttt    4680
cttatagata ttgtgcaata aagctgaagt agaatgtgtg gtttttgcaa atgctttaac    4740
agctgataaa aatttacat ttgtaaaatt aatatattgt actggtacaa aatagtttta    4800
aattatattt taaaaagctt ccaa                                           4824
```

<210> SEQ ID NO 5
<211> LENGTH: 837
<212> TYPE: PRT
<213> ORGANISM: Homo sapiens

<400> SEQUENCE: 5

```
Met Ala Glu Pro Ser Gln Ala Pro Thr Pro Ala Pro Ala Ala Gln Pro
1               5                   10                  15

Arg Pro Leu Gln Ser Pro Ala Pro Ala Pro Thr Pro Thr Pro Ala Pro
                20                  25                  30

Ser Pro Ala Ser Ala Pro Ile Pro Thr Pro Thr Pro Ala Pro Ala Pro
            35                  40                  45

Ala Pro Ala Ala Ala Pro Ala Gly Ser Thr Gly Thr Gly Gly Pro Gly
        50                  55                  60

Val Gly Ser Gly Gly Ala Gly Ser Gly Gly Asp Pro Ala Arg Pro Gly
65                  70                  75                  80

Leu Ser Gln Gln Gln Arg Ala Ser Gln Arg Lys Ala Gln Val Arg Gly
                85                  90                  95
```

```
Leu Pro Arg Ala Lys Lys Leu Glu Lys Leu Gly Val Phe Ser Ala Cys
            100                 105                 110

Lys Ala Asn Glu Thr Cys Lys Cys Asn Gly Trp Lys Asn Pro Lys Pro
            115                 120                 125

Pro Thr Ala Pro Arg Met Asp Leu Gln Gln Pro Ala Ala Asn Leu Ser
            130                 135                 140

Glu Leu Cys Arg Ser Cys Glu His Pro Leu Ala Asp His Val Ser His
145                 150                 155                 160

Leu Glu Asn Val Ser Glu Asp Glu Ile Asn Arg Leu Leu Gly Met Val
                165                 170                 175

Val Asp Val Glu Asn Leu Phe Met Ser Val His Lys Glu Glu Asp Thr
            180                 185                 190

Asp Thr Lys Gln Val Tyr Phe Tyr Leu Phe Lys Leu Leu Arg Lys Cys
            195                 200                 205

Ile Leu Gln Met Thr Arg Pro Val Val Glu Gly Ser Leu Gly Ser Pro
            210                 215                 220

Pro Phe Glu Lys Pro Asn Ile Glu Gln Gly Val Leu Asn Phe Val Gln
225                 230                 235                 240

Tyr Lys Phe Ser His Leu Ala Pro Arg Glu Arg Gln Thr Met Phe Glu
                245                 250                 255

Leu Ser Lys Met Phe Leu Leu Cys Leu Asn Tyr Trp Lys Leu Glu Thr
            260                 265                 270

Pro Ala Gln Phe Arg Gln Arg Ser Gln Ala Glu Asp Val Ala Thr Tyr
            275                 280                 285

Lys Val Asn Tyr Thr Arg Trp Leu Cys Tyr Cys His Val Pro Gln Ser
            290                 295                 300

Cys Asp Ser Leu Pro Arg Tyr Glu Thr Thr His Val Phe Gly Arg Ser
305                 310                 315                 320

Leu Leu Arg Ser Ile Phe Thr Val Thr Arg Arg Gln Leu Leu Glu Lys
                325                 330                 335

Phe Arg Val Glu Lys Asp Lys Leu Val Pro Glu Lys Arg Thr Leu Ile
            340                 345                 350

Leu Thr His Phe Pro Lys Phe Leu Ser Met Leu Glu Glu Glu Ile Tyr
            355                 360                 365

Gly Ala Asn Ser Pro Ile Trp Glu Ser Gly Phe Thr Met Pro Pro Ser
            370                 375                 380

Glu Gly Thr Gln Leu Val Pro Arg Pro Ala Ser Val Ser Ala Ala Val
385                 390                 395                 400

Val Pro Ser Thr Pro Ile Phe Ser Pro Ser Met Gly Gly Gly Ser Asn
                405                 410                 415

Ser Ser Leu Ser Leu Asp Ser Ala Gly Ala Glu Pro Met Pro Gly Glu
            420                 425                 430

Lys Arg Thr Leu Pro Glu Asn Leu Thr Leu Glu Asp Ala Lys Arg Leu
            435                 440                 445

Arg Val Met Gly Asp Ile Pro Met Glu Leu Val Asn Glu Val Met Leu
            450                 455                 460

Thr Ile Thr Asp Pro Ala Ala Met Leu Gly Pro Glu Thr Ser Leu Leu
465                 470                 475                 480

Ser Ala Asn Ala Ala Arg Asp Glu Thr Ala Arg Leu Glu Glu Arg Arg
                485                 490                 495

Gly Ile Ile Glu Phe His Val Ile Gly Asn Ser Leu Thr Pro Lys Ala
            500                 505                 510
```

```
Asn Arg Arg Val Leu Leu Trp Leu Val Gly Leu Gln Asn Val Phe Ser
            515                 520                 525

His Gln Leu Pro Arg Met Pro Lys Glu Tyr Ile Ala Arg Leu Val Phe
        530                 535                 540

Asp Pro Lys His Lys Thr Leu Ala Leu Ile Lys Asp Gly Arg Val Ile
545                 550                 555                 560

Gly Gly Ile Cys Phe Arg Met Phe Pro Thr Gln Gly Phe Thr Glu Ile
                565                 570                 575

Val Phe Cys Ala Val Thr Ser Asn Glu Gln Val Lys Gly Tyr Gly Thr
            580                 585                 590

His Leu Met Asn His Leu Lys Glu Tyr His Leu Lys His Asn Ile Leu
        595                 600                 605

Tyr Phe Leu Thr Tyr Ala Asp Glu Tyr Ala Ile Gly Tyr Phe Lys Lys
    610                 615                 620

Gln Gly Phe Ser Lys Asp Ile Lys Val Pro Lys Ser Arg Tyr Leu Gly
625                 630                 635                 640

Tyr Ile Lys Asp Tyr Glu Gly Ala Thr Leu Met Glu Cys Glu Leu Asn
                645                 650                 655

Pro Arg Ile Pro Tyr Thr Glu Leu Ser His Ile Ile Lys Lys Gln Lys
            660                 665                 670

Glu Ile Ile Lys Lys Leu Ile Glu Arg Lys Gln Ala Gln Ile Arg Lys
        675                 680                 685

Val Tyr Pro Gly Leu Ser Cys Phe Lys Glu Gly Val Arg Gln Ile Pro
    690                 695                 700

Val Glu Ser Val Pro Gly Ile Arg Glu Thr Gly Trp Lys Pro Leu Gly
705                 710                 715                 720

Lys Glu Lys Gly Lys Glu Leu Lys Asp Pro Asp Gln Leu Tyr Thr Thr
                725                 730                 735

Leu Lys Asn Leu Leu Ala Gln Ile Lys Ser His Pro Ser Ala Trp Pro
            740                 745                 750

Phe Met Glu Pro Val Lys Lys Ser Glu Ala Pro Asp Tyr Tyr Glu Val
        755                 760                 765

Ile Arg Phe Pro Ile Asp Leu Lys Thr Met Thr Glu Arg Leu Arg Ser
    770                 775                 780

Arg Tyr Tyr Val Thr Arg Lys Leu Phe Val Ala Asp Leu Gln Arg Val
785                 790                 795                 800

Ile Ala Asn Cys Arg Glu Tyr Asn Pro Pro Asp Ser Glu Tyr Cys Arg
                805                 810                 815

Cys Ala Ser Ala Leu Glu Lys Phe Phe Tyr Phe Lys Leu Lys Glu Gly
            820                 825                 830

Gly Leu Ile Asp Lys
        835

<210> SEQ ID NO 6
<211> LENGTH: 3127
<212> TYPE: DNA
<213> ORGANISM: Homo sapiens

<400> SEQUENCE: 6
ggttgcccat gcggccctag ggctgggagc gcggcgccgc tctccgctgc gggggaggcc    60
atggcggaac cttcccaggc ccgaccccg gccccggctg cgcagccccg gccccttcag   120
tccccagccc ctgccccaac tccgactcct gcacccagcc cggcttcagc ccgattccg   180 actcccaccc cggcaccagc ccctgcccca gctgcagccc cagccggcag cacagggact   240
```

```
gggggccccg gggtaggaag tggggggccc gggagcgggg gggatccggc tcgacctggc    300
ctgagccagc agcagcgcgc cagtcagagg aaggcgcaag tccggggggct gccgcgcgcc   360 aagaagcttg agaagctagg ggtcttctcg gcttgcaagg ccaatgaaac ctgtaagtgt    420
aatggctgga aaaaccccaa gcccccccact gcaccccgca tggatctgca gcagccagct   480
gccaacctga gtgagctgtg ccgcagttgt gagcacccct tggctgacca cgtatcccac    540
ttggagaatg tgtcagagga tgagataaac cgactgctgg ggatggtggt ggatgtggag    600
aatctcttca tgtctgttca caaggaagag gacacagaca ccaagcaggt ctatttctac    660
ctcttcaagc tactgcggaa atgcatcctg cagatgaccc ggcctgtggt ggaggggtcc    720
ctgggcagcc ctccatttga gaaacctaat attgagcagg gtgtgctgaa ctttgtgcag    780
tacaagttta gtcacctggc tccccgggag cggcagacga tgttcgagct ctcaaagatg    840
ttcttgctct gccttaacta ctggaagctt gagacacctg cccagtttcg gcagaggtct    900
caggctgagg acgtggctac ctacaaggtc aattacacca gatggctctg ttactgccac    960
gtgccccaga gctgtgatag cctccccgc tacgaaacca ctcatgtctt tgggcgaagc    1020
cttctccggt ccattttcac cgttacccgc cggcagctgc tggaaaagtt ccgagtggag    1080
aaggacaaat tggtgcccga gaagaggacc ctcatcctca ctcacttccc caaattcctg    1140
tccatgctgg aggaggagat ctatgggggca aactctccaa tctggagtc aggcttcacc    1200 atgccacct cagaggggac acagctggtt ccccggccag cttcagtcag tgcagcggtt    1260
gttcccagca ccccccatctt cagccccagc atgggtgggg gcagcaacag ctccctgagt    1320
ctggattctg caggggccga gcctatgcca ggcgagaaga ggacgctccc agagaacctg    1380
accctggagg atgccaagcg gctccgtgtg atgggtgaca tccccatgga gctggtcaat    1440
gaggtcatgc tgaccatcac tgaccctgct gccatgctgg ggcctgagac gagcctgctt    1500
tcggccaatg cggcccggga tgagacagcc cgcctggagg agcgccgcgg catcatcgag    1560
ttccatgtca tcggcaactc actgacgccc aaggccaacc ggcgggtgtt gctgtggctc    1620
gtggggctgc agaatgtctt ttcccaccag ctgccgcgca tgcctaagga gtatatcgcc    1680
cgcctcgtct ttgaccccaa gcacaagact ctggccttga tcaaggatgg gcgggtcatc    1740
ggtggcatct gcttccgcat gtttcccacc cagggcttca cggagattgt cttctgtgct    1800
gtcacctcga atgagcaggt caagggttat gggacccacc tgatgaacca cctgaaggag    1860
tatcacatca agcacaacat tctctacttc ctcacctacg ccgacgagta cgccatcggc    1920
tacttcaaaa agcagggttt ctccaaggac atcaaggtgc ccaagagccg ctacctgggc    1980
tacatcaagg actacgaggg agcgacgctg atggagtgtg agctgaatcc ccgcatcccc    2040 tacacgagc tgtcccacat catcaagaag cagaaagaga tcatcaagaa gctgattgag    2100
cgcaaacagg cccagatccg caaggtctac ccggggctca gctgcttcaa ggagggcgtg    2160
aggcagatcc ctgtggagag cgttcctggc attcgagaga caggctggaa gccattgggg    2220
aaggagaagg ggaaggagct gaaggacccc gaccagctct acaccaaccct caaaaacctg    2280 ctggcccaaa tcaagtctca ccccagtgcc tggcccttca tggagcctgt gaagaagtcg    2340
gaggcccctg actactacga ggtcatccgc ttccccattg acctgaagac catgactgag    2400
cggctgcgaa gccgctacta cgtgacccgg aagctctttg tggccgacct gcagcgggtc    2460
atcgccaact gtcgcgagta caaccccccg gacagcgagt actgccgctg tgccagcgcc    2520
ctggagaagt tcttctactt caagctcaag gagggaggcc tcattgacaa gtaggccat    2580 ctttgggccg cagccctgac ctggaatgtc tccacctcgg attctgatct gatccttagg    2640
```

```
gggtgccctg gccccacgga cccgactcag cttgagacac tccagccaag ggtcctccgg    2700
acccgatcct gcagctcttt ctggaccttc aggcaccccc aagcgtgcag ctctgtccca    2760
gccttcactg tgtgtgagag gtctcctggg ttggggccca gcccctctag agtagctggt    2820
ggccagggat gaaccttgcc cagccgtggt ggcccccagg cctggtcccc aagagctttg    2880
gaggcttgga ttcctgggcc tggcccaggt ggctgtttcc ctgaggacca gaactgctca    2940
ttttagcttg agtgatggct tcaggggttg gaagttcagc ccaaactgaa ggggccatg    3000 ccttgtccag cactgttctg tcagtctccc ccaggggtgg ggggtatggg gaccattcat    3060
tccctggcat taatcccta gagggaataa taaagctttt tatttctctg tgaaaaaaaa    3120
aaaaaaa                                                              3127
```